(12) United States Patent
Asmus et al.

(10) Patent No.: US 8,042,251 B2
(45) Date of Patent: Oct. 25, 2011

(54) SYSTEMS AND METHODS FOR HEATING AND COOLING DURING STENT CRIMPING

(75) Inventors: Bruce H. Asmus, Minnetonka, MN (US); Brian R. Butler, Monticello, MN (US); Ray Adney, Coon Rapids, MN (US); Timothy G. J. Ehr, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 826 days.

(21) Appl. No.: 12/124,951

(22) Filed: May 21, 2008

(65) Prior Publication Data
US 2009/0292347 A1   Nov. 26, 2009

(51) Int. Cl.
B21D 39/00 (2006.01)
A61F 2/84 (2006.01)

(52) U.S. Cl. ..................... 29/516; 623/1.11

(58) Field of Classification Search ........... 29/516, 29/515, 506, 507, 508, 505, 522, 523, 800; 623/1.11, 1.12, 1.21; 606/194, 191, 192, 606/198, 108; 128/898
See application file for complete search history.

(56) References Cited

U.S. PATENT DOCUMENTS

| | | | |
|---|---|---|---|
| 5,836,965 A | 11/1998 | Jendersee et al. | |
| 5,913,871 A | 6/1999 | Werneth et al. | |
| 5,976,155 A | 11/1999 | Foreman et al. | |
| 5,976,181 A | 11/1999 | Whelan et al. | |
| 6,063,092 A | 5/2000 | Shin | |
| 6,066,156 A * | 5/2000 | Yan | 606/192 |
| 6,077,273 A | 6/2000 | Euteneuer et al. | |
| 6,099,563 A | 8/2000 | Zhong | |
| 6,159,229 A | 12/2000 | Jendersee et al. | |
| 6,187,013 B1 | 2/2001 | Stoltze et al. | |
| 6,231,600 B1 | 5/2001 | Zhong | |
| 6,309,402 B1 | 10/2001 | Jendersee et al. | |
| 6,360,577 B2 | 3/2002 | Austin | |
| 6,568,235 B1 | 5/2003 | Kokish | |
| 6,569,195 B2 | 5/2003 | Yang et al. | |
| 6,589,546 B2 | 7/2003 | Kamath et al. | |
| 6,651,478 B1 | 11/2003 | Kokish | |
| 6,666,880 B1 | 12/2003 | Chiu et al. | |
| 6,730,117 B1 | 5/2004 | Tseng et al. | |
| 6,776,793 B2 | 8/2004 | Brown et al. | |
| 6,823,576 B2 | 11/2004 | Austin | |
| 6,840,081 B2 | 1/2005 | Kokish | |
| 6,915,560 B2 | 7/2005 | Austin | |
| 6,945,993 B2 | 9/2005 | Kveen et al. | |

(Continued)

FOREIGN PATENT DOCUMENTS
EP      1295570      3/2003

(Continued)

Primary Examiner — John C Hong
(74) Attorney, Agent, or Firm — Seager, Tufte & Wickhem, LLC

(57) ABSTRACT

Methods of heating and cooling during a crimping process are disclosed. One method includes providing a cooling source to cool the stent and/or drug eluting coating of the stent while crimping the stent onto the balloon, and providing a heating source to heat the balloon while crimping the stent onto the balloon. Another method includes introducing a cooling fluid through a passage in one or more of the plurality of crimping elements of the crimping apparatus to cool the crimping elements while crimping the stent onto the balloon, and introducing a heating fluid through the elongate shaft of the balloon catheter to heat the balloon while crimping the stent onto the balloon.

34 Claims, 26 Drawing Sheets

U.S. PATENT DOCUMENTS

| | | |
|---|---|---|
| 6,948,223 B2 | 9/2005 | Shortt |
| 6,958,073 B2 * | 10/2005 | Rogers et al. .................. 606/194 |
| 6,981,986 B1 | 1/2006 | Brown et al. |
| 6,986,785 B2 | 1/2006 | O'Shaughnessy et al. |
| 7,021,114 B2 | 4/2006 | Perreault |
| 7,063,884 B2 | 6/2006 | Hossainy et al. |
| 7,143,625 B2 | 12/2006 | Edin |
| 2002/0049492 A1 | 4/2002 | Lashinski et al. |
| 2003/0032999 A1 | 2/2003 | Huang |
| 2003/0208254 A1 | 11/2003 | Shortt |
| 2004/0078953 A1 | 4/2004 | Spilka |
| 2004/0098078 A1 | 5/2004 | Stoltze et al. |
| 2004/0148007 A1 | 7/2004 | Jackson et al. |
| 2004/0181236 A1 | 9/2004 | Eidenschink et al. |
| 2004/0193177 A1 | 9/2004 | Houghton et al. |
| 2005/0118344 A1 | 6/2005 | Pacetti |
| 2005/0119720 A1 | 6/2005 | Gale et al. |
| 2005/0154450 A1 | 7/2005 | Larson et al. |
| 2006/0009832 A1 | 1/2006 | Fisher |
| 2006/0123874 A1 | 6/2006 | Motsenbocker |
| 2006/0288561 A1 | 12/2006 | Roach et al. |
| 2007/0079494 A1 | 4/2007 | Serrano |
| 2008/0021543 A1 | 1/2008 | Shrivastava |

FOREIGN PATENT DOCUMENTS

| | | |
|---|---|---|
| EP | 1466570 | 10/2004 |
| WO | 03092548 | 11/2003 |
| WO | 2005053937 | 6/2005 |
| WO | 2005092574 A1 | 6/2005 |

* cited by examiner

SYSTEMS AND METHODS FOR HEATING AND COOLING DURING STENT CRIMPING

FIELD

The present disclosure relates generally to the field of crimping stents or other medical devices onto a delivery device. More specifically, the present disclosure pertains to systems and methods for heating and cooling a stent and stent delivery device during stent crimping.

BACKGROUND

Medical devices such as stents, stent grafts, and vena cava filters are often utilized in combination with a delivery device for placement at a desired location within the body. A medical prosthesis such as a stent, for example, may be loaded onto a stent delivery device such as a balloon catheter and then introduced into the lumen of a body vessel in a configuration having a reduced diameter. Once delivered to a target location within the body, the stent may then be expanded to an enlarged configuration within the vessel to support and reinforce the vessel wall while maintaining the vessel in an open, unobstructed condition. In some medical procedures such as a percutaneous transluminal coronary angioplasty (PTCA), for example, the stent may be deployed and expanded within a vessel adjacent to the location where a lesion has been removed to prevent restenosis or prolapse of the vessel at that region. The stent may be either self-expanding, or alternatively, may be mechanically expanded by the inflation of a balloon on the delivery device.

Inflation expandable stents are typically secured to the balloon of a balloon catheter in a reduced diameter configuration or profile prior to their use. In some techniques, for example, the stents are loaded onto the balloon and then inserted into a crimping device which applies an inwardly directed radial force to the stent to reduce the diameter of the stent around the balloon. In some techniques, the balloon material may be heated to an elevated temperature, such as greater than the glass transition temperature of the balloon material, causing the balloon material to soften and thus more easily conform to the contours of the stent. However, elevated temperatures have been found to adversely affect the performance and/or integrity of the drug eluting coating on the stent.

Therefore, there is an ongoing desire to provide alternative methods and techniques to crimp a stent onto a balloon of a balloon catheter. Furthermore, there is an ongoing desire to provide alternative arrangements of systems, assemblies and apparatus for crimping a stent onto a balloon of a balloon catheter.

BRIEF SUMMARY

The disclosure is related to several alternative designs, materials and methods of stent crimping and/or stent crimping systems, assemblies and apparatus.

Accordingly, one illustrative embodiment is a method of crimping a stent onto a balloon of a balloon catheter. The method comprises providing a crimping apparatus including a plurality of crimping elements forming a crimping lumen having a diameter, wherein the plurality of crimping elements are actuatable to alter the diameter of the crimping lumen. A balloon catheter including an elongate shaft and an inflation balloon secured to a distal region of the elongate shaft is also provided. A stent is positioned around the balloon of the balloon catheter. The stent and the balloon of the balloon catheter are situated within the crimping lumen. The stent is then crimped onto the balloon of the balloon catheter with the crimping apparatus. While crimping the stent onto the balloon of the balloon catheter, the balloon is heated to a temperature greater than 40° C. and the crimping elements are maintained at a temperature less than 40° C.

Another illustrative embodiment is a method of crimping a stent onto a balloon of a balloon catheter comprising providing a crimping apparatus including a plurality of crimping elements forming a crimping lumen having a diameter, wherein the plurality of crimping elements are actuatable to alter the diameter of the crimping lumen. A balloon catheter including an elongate shaft and an inflation balloon secured to a distal region of the elongate shaft is also provided. A stent is positioned around the balloon of the balloon catheter. The stent and the balloon of the balloon catheter are situated within the crimping lumen. The stent is then crimped onto the balloon of the balloon catheter with the crimping apparatus. While crimping the stent, one or more of the plurality of crimping elements of the crimping apparatus are cooled, and the balloon of the balloon catheter is heated.

Yet another illustrative embodiment is a stent crimping system for crimping a stent onto a balloon of a balloon catheter. The stent crimping system includes a crimping apparatus including a plurality of actuatable crimping elements defining a crimping lumen, a balloon catheter including an elongate shaft and an inflation balloon, and a stent disposed about the inflation balloon. The stent crimping system also includes a means for transferring heat energy to the inflation balloon such that the inflation balloon has a temperature greater than 40° C., and a means for transferring heat energy from the plurality of crimping elements such that the plurality of crimping elements have a temperature less than 40° C.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
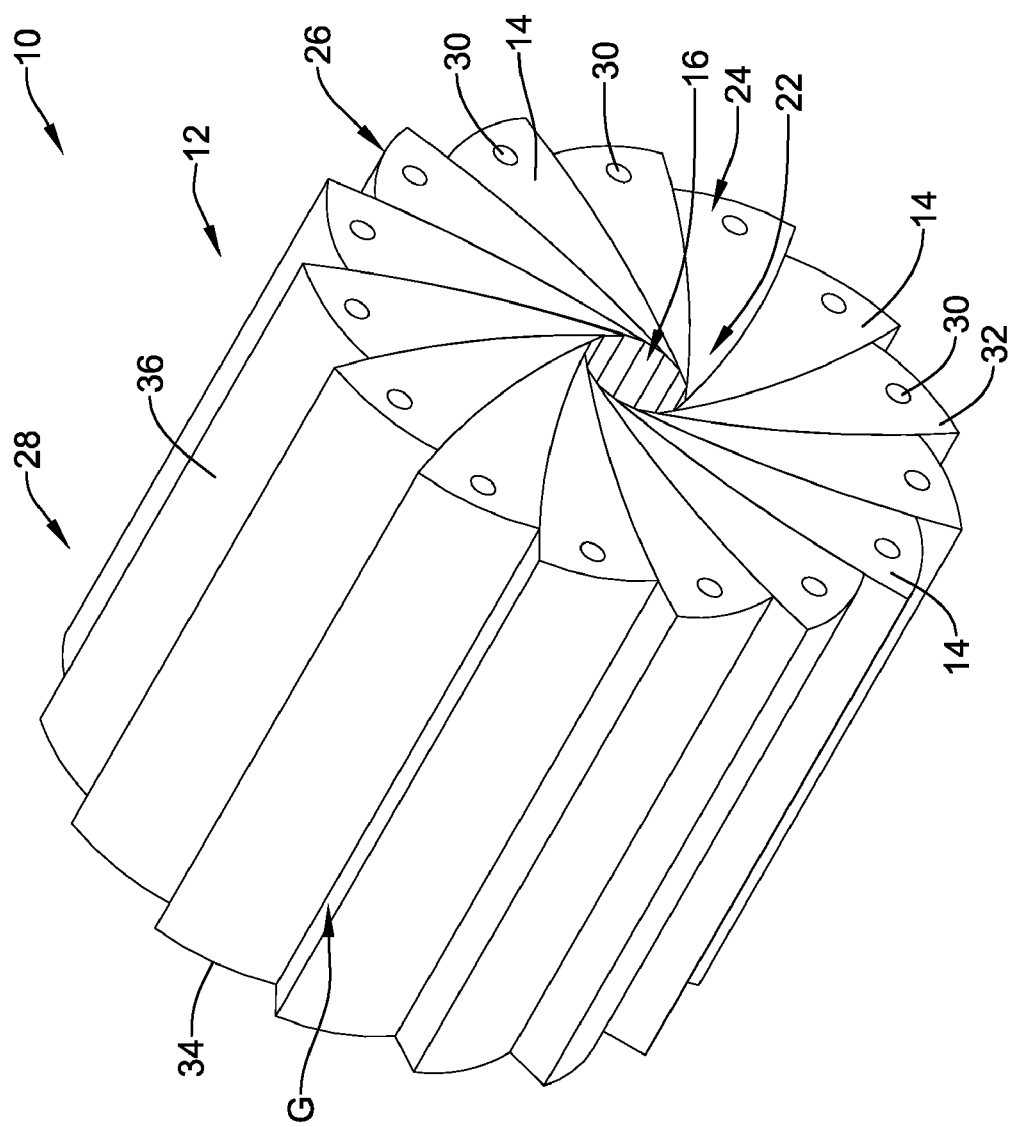
FIG. 1 is a perspective view of an illustrative crimping apparatus for crimping a stent onto a balloon of a balloon catheter.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the terms "to cool" "cooled" or "cooling", as used in their verb tense, are intended to refer to removing or transferring heat energy from a body. For instance, the terms "to cool" "cooled" or "cooling", as used in their verb tense, may refer to removing or transferring heat energy from a body such that the temperature of the body is reduced from a higher temperature to a lower temperature, or the terms "to cool" "cooled" or "cooling", as used in their verb tense, may refer to removing or transferring heat energy from a body such that the temperature of the body is maintained as heat energy is added or transferred to the body from an external source.

As used in this specification and the appended claims, the terms "to heat" "heated" or "heating" as used in their verb tense, are intended to refer to adding or transferring heat energy to a body. For instance, the terms "to heat" "heated" or "heating", as used in their verb tense, may refer to adding or transferring heat energy to a body such that the temperature of the body is increased from a lower temperature to a higher temperature, or the terms "to heat" "heated" or "heating", as used in their verb tense, may refer to adding or transferring heat energy to a body such that the temperature of the body is maintained as heat energy is removed or transferred from the body to another body.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, an illustrative crimping apparatus 10 in accordance with an illustrative embodiment will now be described. The crimping apparatus 10, illustratively a stent crimping and coating apparatus for crimping a stent onto the balloon of a stent delivery catheter, can include a crimping section 12 having a number of movable blades 14 radially disposed about a central crimping lumen 16. In the illustrative embodiment depicted in FIG. 1, for example, the crimping section 12 includes fifteen blades radially disposed about the lumen 16. The crimping apparatus 10 may be equipped with a greater or lesser number of crimping blades 14, however, depending on the size and configuration of the stent to be inserted therein. The crimping blades 14 may be made of a suitably hard material such as a hardened steel or ceramic, although other materials are possible. The crimping blades 14 can be configured to move independently of each other or in unison, and can be configured to collectively contract inwardly towards the central axis of the crimping lumen 16 and retract outwardly away from the central axis of the lumen 16 in order to adjust the size of the crimping lumen 16. When contracted, each of the crimping blades 14 can be configured to provide an inwardly directed radial force to the inserted stent assembly disposed in the crimping lumen 16. Movement of the crimping blades 14 can be accomplished using an actuation mechanism (not shown), which can include a number of levers, cams, bearings, connecting links, rods, cylinders, motors, gears, or the like. In use, the crimping apparatus 10 may be used to reduce the diameter of a stent inserted within the crimping lumen 16 and/or may be used to crimp the stent onto another member such as a stent delivery catheter or introducer.

In some embodiments, the crimping apparatus 10 may be equipped with a loading platform (not shown) that can be used to facilitate the insertion of the stent and stent delivery catheter into the crimping lumen 16 during crimping and, in some cases, coating. The platform may be configured to support the stent and/or stent delivery catheter during loading of the assembly into the crimping lumen 16 for crimping. In some embodiments, for example, the position of the platform can be adjusted to ensure that the stent and/or stent delivery catheter are loaded centrally within the crimping lumen 16. Such central loading may be beneficial, for example, to ensure that the radial forces exerted on the stent are substantially uniform during the crimping process.

Each of the crimping blades 14 can include an inner section 22 (e.g., a radially inward portion), a peripheral section 24

(e.g., a radially outward portion), and a length extending from a first end 26 of the apparatus 10 to a second end 28 thereof. The crimping blades 14 may be radially arranged about a reference circle to form an adjustable crimping aperture, such as an iris. In some embodiments, the crimping blades 14 can be configured and arranged such that each blade 14 has only a single point which lies on the circumference of the reference circle prior to movement of the blade and is moved along a radius of the reference circle upon movement of the blade 14.

The crimping blades 14 may have a length that is equal to or greater than the length of the stent to be inserted into the crimping lumen 16. In some embodiments, for example, the length of the crimping blades 14 may be about 5 cm to 20 cm in length, and more specifically, about 10 cm to 15 cm in length. The length of the crimping blades 14 may deviate from these dimensions, however, depending on the particular configuration of the stent or other medical device to be crimped, the length of crimping desired, as well as other factors. Typically, the crimping blades 14 will have a length as long as or longer than the medical device (e.g., stent) positioned in the crimping lumen 16 such that the medical device is reduced uniformly in size along its length. In crimping stents, for example, the blades 14 will typically have a length at least as long as the axial length of the stent, thus ensuring a more uniform crimp along the length of the stent.

The crimping blades 14 may be separated from each other by a small gap G, which may extend along the entire length of the blade 14. In use, the small gap G between each of the blades 14 allows the blades 14 to slide relative to each other. In certain embodiments, the gap G can be configured so that the blades 14 slide relative to one another without an undue amount of friction. The amount of spacing G between the crimping blades 14 may depend upon several factors, including the number of blades 14, the size and shape of the blades 14, the desired size of the crimping lumen 16, and the size of the stent assembly.

The crimping lumen 16 may extend longitudinally along an axis from the first end 26 of the apparatus 10 to the second end 28 thereof. Alternatively, and in other embodiments, the crimping lumen 16 may extend longitudinally from the first end 26 of the apparatus 10 toward the second end 28 but terminate before the second end 28.

An illustrative crimping apparatus which may be modified in view of this disclosure is described in U.S. Pat. No. 6,823,576, herein incorporated by reference in its entirety. However, it is noted that any other crimping apparatus for radially contracting the stent onto a balloon of a balloon catheter may be modified in view of this disclosure, if desired.

The crimping apparatus 10 may include a means for cooling the crimping blades 14 and/or at least a portion of a stent, such as a coating of the stent and/or the interconnected struts of the stent, placed within the crimping apparatus 10. For example, as shown in FIG. 1, each of the crimping blades 14 may include a first port (e.g., entry port) 30 providing access to an interior passage extending within the crimping blade 14. In some embodiments, the first port 30 may be located on the first end surface 32 of the crimping blade 14 proximate the first end 26, may be located on the second end surface 34 (shown in FIG. 2) of the crimping blade 14 proximate the second end 28, or may be located on the peripheral surface 36 of the crimping blade 14.

The crimping blade 14 may also include a second port (e.g., exit port) 38 (see FIG. 2) providing access to an interior passage extending within the crimping blade 14. In some embodiments, the second port 38 may be located on the second end surface 34 of the crimping blade 14 proximate the second end 28, may be located on the first end surface 32 of the crimping blade 14 proximate the first end 26, or may be located on the peripheral surface 36 of the crimping blade 14.

Figure 2:
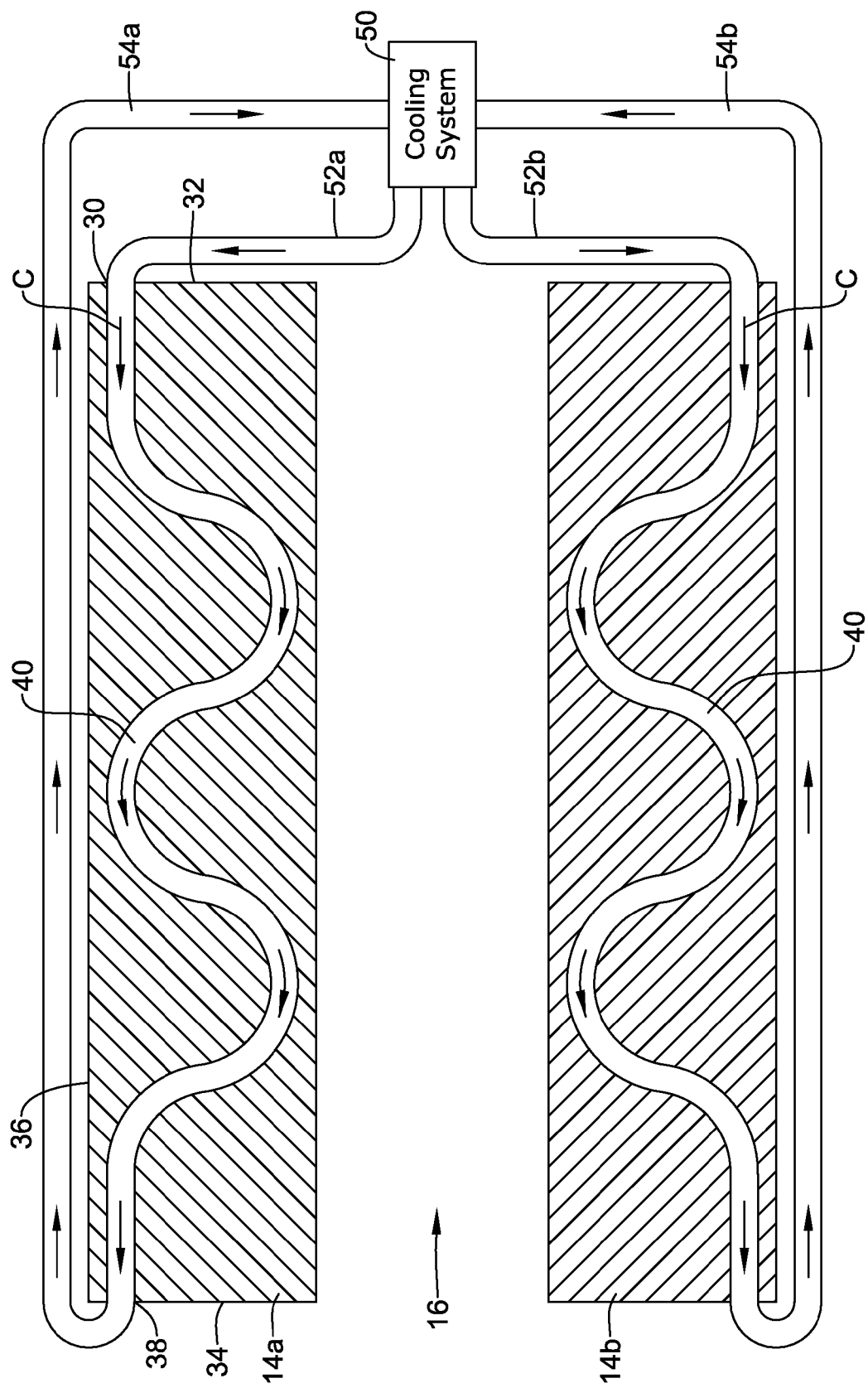
FIG. 2 is a cross-sectional view of a crimping apparatus including a cooling system.

As further illustrated in FIG. 2, the first port 30 and/or the second port 38 provide access to a passage 40 extending through the interior of the crimping blades 14. Thus, the passage 40 may pass through the interior of the crimping blade 14 from the first port 30 to the second port 38. The passage 40 may take any desired path through the crimping blade 14. For instance, as shown in FIG. 2, the passage 40 may pass through the crimping blade 14 along a serpentine, or back-and-forth, path in some embodiments from the first port 30 to the second port 38. In other embodiments, the passage 40 may be substantially straight, passing between the first port 30 and the second port 38 along a straight axis. Yet, in other embodiments the passage 40 may extend between the first port 30 and the second port 38 along another desired path.

As shown in FIG. 2, the crimping system including the crimping apparatus 10 may also include a cooling system 50 which is in fluid communication with the passage 40 passing through one or more crimping blades 14 of the crimping apparatus 10. For example, in some embodiments the cooling system 50 may be in fluid communication with a passage 40 passing through each of the crimping blades 14 of the crimping apparatus 10, or a subset of the crimping blades 14 of the crimping apparatus 10. The cooling system 50 may help cool the crimping blades 14 during a crimping process.

For instance, a fluid inlet conduit 52a of the cooling system 50 may be coupled to the inlet port 30 of a first crimping blade 14a of the crimping apparatus 10, such that the fluid inlet conduit 52a is in fluid communication with the passage 40 of the first crimping blade 14a. Additionally, a fluid inlet conduit 52b of the cooling system 50 may be coupled to the inlet port 30 of a second crimping blade 14b of the crimping apparatus 10, such that the fluid inlet conduit 52b is in fluid communication with the passage 40 of the second crimping blade 14b. Additional fluid inlet conduits 52 may be coupled to inlet ports 30 of additional crimping blades 14 of the crimping apparatus 10 as desired. For instance, in some embodiments a fluid inlet conduit 52 of the cooling system 50 may be coupled to an inlet port 30 of each crimping blade 14 of the crimping apparatus 10.

Furthermore, a fluid outlet conduit 54a of the cooling system 50 may be coupled to the outlet port 38 of the first crimping blade 14a of the crimping apparatus 10, such that the fluid outlet conduit 54a is in fluid communication with the passage 40 of the first crimping blade 14a. Additionally, a fluid outlet conduit 54b of the cooling system 50 may be coupled to the outlet port 38 of the second crimping blade 14b of the crimping apparatus 10, such that the fluid outlet conduit 54b is in fluid communication with the passage 40 of the second crimping blade 14b. Additional fluid outlet conduits 54 may be coupled to outlet ports 38 of additional crimping blades 14 of the crimping apparatus 10 as desired. For instance, in some embodiments a fluid outlet conduit 54 of the cooling system 50 may be coupled to an outlet port 38 of each crimping blade 14 of the crimping apparatus 10.

The fluid inlet conduits 52 provide a fluid pathway from the cooling system 50 to the passage 40 of the crimping blades 14 of the crimping apparatus 10 for introducing a cooling fluid (e.g., a cooled fluid or a coolant) into the passage 40 of the crimping blades 14, and the fluid outlet conduits 54 provide a fluid pathway from the passage 40 of the crimping blades 14 of the crimping apparatus 10 to the cooling system 50 for directing the fluid out of the passage 40 of the crimping blades 14. Thus, it can be seen that a fluid (e.g., a cooled fluid or a coolant) may be circulated through the passage 40 of the crimping blades 14 via the inlet conduit 52 and the outlet conduit 54 coupled between the cooling system 50 and the crimping blades 14.

Passing a cooling fluid C (e.g., a cooled fluid or a coolant) through the passage 40 of the crimping blades may extract heat from (i.e., cool) the crimping blades 14 during a crimping process. For example, heat may be transferred from the crimping blades 14 to the cooling fluid C by conduction as the cooling fluid C is passed through the passage 40 of the crimping blades 14.

Other embodiments may include alternate cooling means. For example, a cooled body (e.g., a body at a lower temperature than the crimping blades 14 and/or lower than the temperature reached by the balloon 66, for example, a body having a temperature less than 40° C., less than 30° C., less than 20° C., less than 15° C, less than 10° C., less than 5° C., or less than 0° C.) may be placed in contact with one or more crimping blades 14 of the crimping apparatus 10 to conductively draw heat from the crimping blades 14. In some embodiments, the crimping apparatus 10 including the crimping blades 14 may be placed in a cooled environment (e.g., a room having an air temperature of less than the crimping blades 14 and/or less than the temperature reached by the balloon 66, for example, an ambient environment having a temperature less than 15° C., less than 10° C., less than 5° C., or less than 0° C.).

Figure 3A:
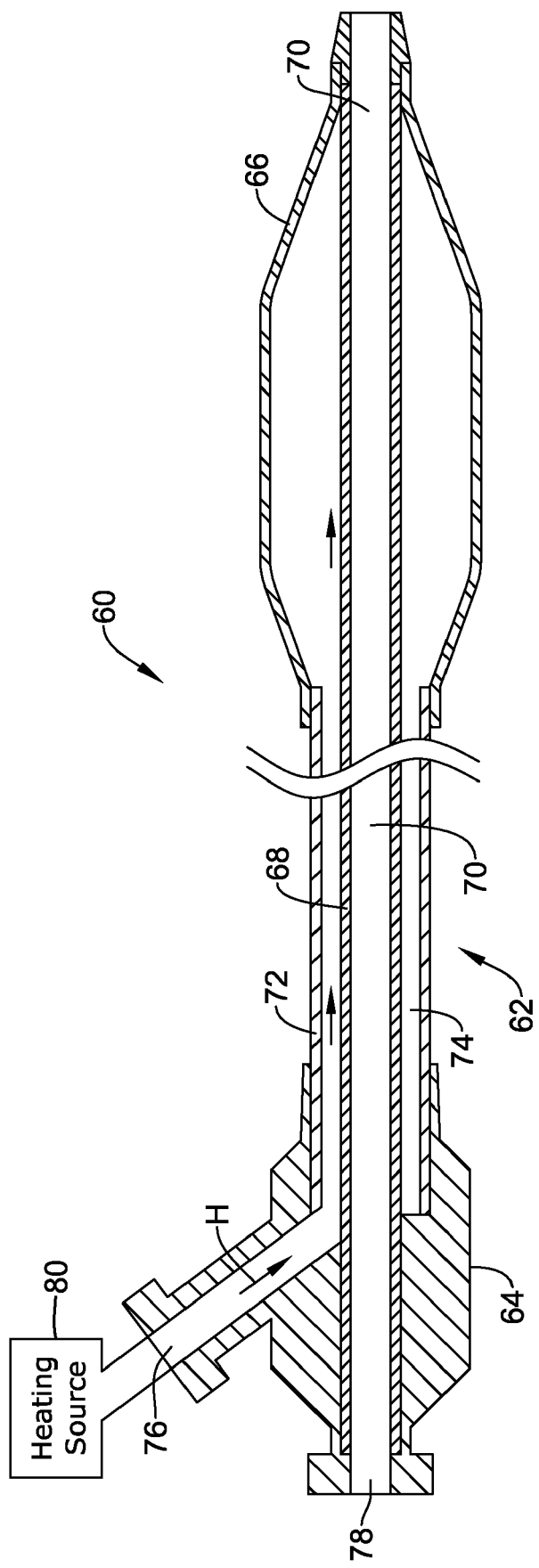
FIG. 3A is a cross-sectional view of a balloon catheter including a heating source for heating the balloon.

A balloon catheter 60 including an elongate shaft 62, a hub assembly 64 coupled to the proximal end of the elongate shaft 62 and an inflation balloon 66 secured to the distal end of the elongate shaft 62 is shown in FIG. 3A. As shown in FIG. 3A, the elongate shaft 62 may include an inner tubular member 68 defining a guidewire lumen 70 and an outer tubular member 72 disposed about the inner tubular member 68 defining an inflation lumen 74 between the inner tubular member 68 and the outer tubular member 72. The inflation lumen 74 may be in fluid communication with the interior of the inflation balloon 66. The hub assembly 64 may include an inflation port 76 in fluid communication with the inflation lumen 74 and the inflation balloon 66, and the hub assembly 64 may include a guidewire port 78 in fluid communication with the guidewire lumen 70. Although the balloon catheter 60 is illustrated as an over-the-wire (OTW) balloon catheter having a guidewire lumen 70 extending from the proximal end of the catheter to the distal end of the catheter, in other embodiments, the balloon catheter 60 may be a single-operator exchange (SOE) balloon catheter in which the guidewire lumen 70 extends from the distal end of the catheter 60 to an exit port at a location distal of the proximal end of the catheter 60, or the balloon catheter 60 may be of another configuration. In yet other embodiments, the balloon catheter 60 may not include a guidewire lumen. For example, in embodiments in which the balloon catheter 60 is a fixed-wire and/or an on-the-wire balloon catheter, the balloon catheter 60 may not include a guidewire lumen.

The system may include a means for heating the balloon 66 of the balloon catheter 60. For example, as shown in FIG. 3A, a heating source 80 may be coupled to the inflation port 76 of the hub assembly 64 during a crimping process. The heating source 80 may direct heat to the balloon 66 to heat the material of the balloon 66 to a desired temperature during a crimping process. For instance, during a crimping process, a heating fluid H may be directed through the inflation lumen 74 to the interior of the inflation balloon 66 to heat the balloon material to an elevated temperature greater than room temperature (e.g., greater than about 22° C.) during a crimping process. In some embodiments, the heating fluid H may heat the balloon material to an elevated temperature equal to or greater than a glass transition temperature of the balloon material. For instance, in some embodiments, the balloon material may be heated to a temperature greater than 40° C., greater that 45° C., or greater that 50° C.

Figure 3B:
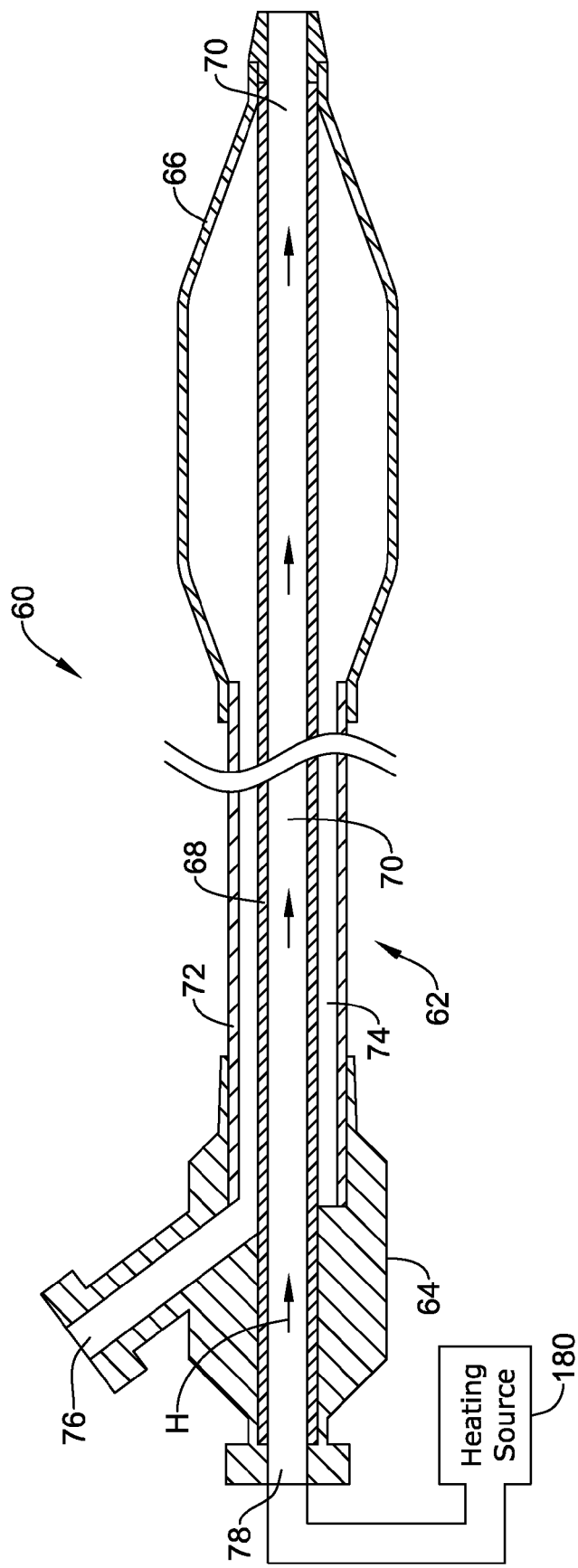
FIG. 3B is a cross-sectional view of a balloon catheter including a heating source for heating the balloon.

In another embodiment, as shown in FIG. 3B, a heating source 180 may be coupled to the guidewire port 78 of the hub assembly 64 during a crimping process. The heating source 180 may direct heat to the balloon 66 to heat the material of the balloon 66 to a desired temperature during a crimping process. For instance, during a crimping process, a heating fluid H may be directed through the guidewire lumen 70 to heat the balloon material to an elevated temperature greater than room temperature (e.g., greater than about 22° C.) during a crimping process. In some embodiments, the heating fluid H may heat the balloon material to an elevated temperature equal to or greater than a glass transition temperature of the balloon material. For instance, in some embodiments, the balloon material may be heated to a temperature greater than 40° C., greater that 45° C., or greater that 50° C.

It is noted, however, that in other embodiments disclosed herein, the balloon material may be heated to an elevated temperature greater than room temperature (e.g., greater than about 22° C.) during a crimping process by other means. For example, in some embodiments a heated mandrel may be disposed through the guidewire lumen 70 of the balloon catheter 60. In other embodiments electromagnetic waves may be used to heat the material of the balloon 66. For example, a moisture rich environment may be established within the interior of the balloon 66, and the balloon 66 may be exposed to microwave energy to heat the balloon material during a crimping process. Alternatively, the balloon 66 may include a moisture rich material, or other material responsive to microwave energy, to heat the balloon material during a crimping process by exposing the balloon 66 to microwave energy during the crimping process. In still other embodiments, the crimping apparatus 10 and/or balloon catheter 60 may be included in a heat pump system, or other thermodynamic cycle, to provide the desired heating of the balloon 66 and/or cooling of the crimping blades 14.

Figure 4:
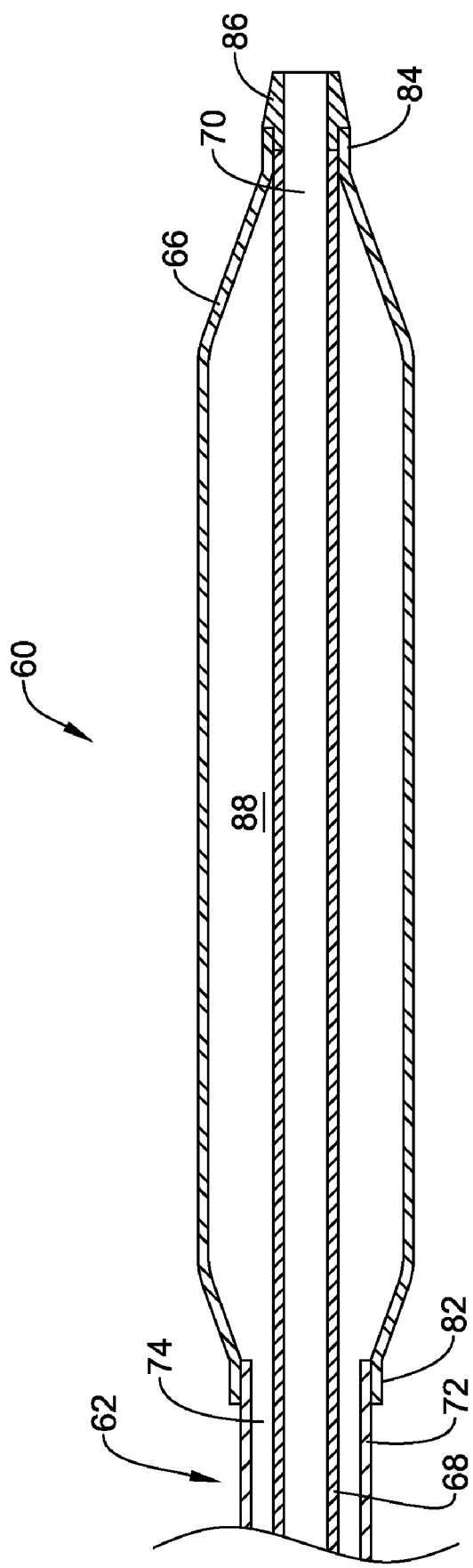
FIG. 4 is a cross-sectional view of the distal portion of a balloon catheter.

The distal portion of the balloon catheter 60 is further illustrated in FIG. 4. As shown in FIG. 4, the inflation balloon 66 may include a proximal waist 82 secured (e.g., adhesively bonded or thermally bonded) to the distal end of the outer tubular member 72 of the elongate shaft 62, and the inflation balloon 66 may include a distal waist 84 secured (e.g., adhesively bonded or thermally bonded) to the distal end of the inner tubular member 68 proximate a distal tip 86. Thus, the inflation lumen 74 may be in fluid communication with the interior 88 of the inflation balloon 66. The inner tubular member 68 may extend through the inflation balloon 66, defining a guidewire lumen 70 extending from the distal tip 86 to an exit port proximal of the inflation balloon 66.

Figure 5A:
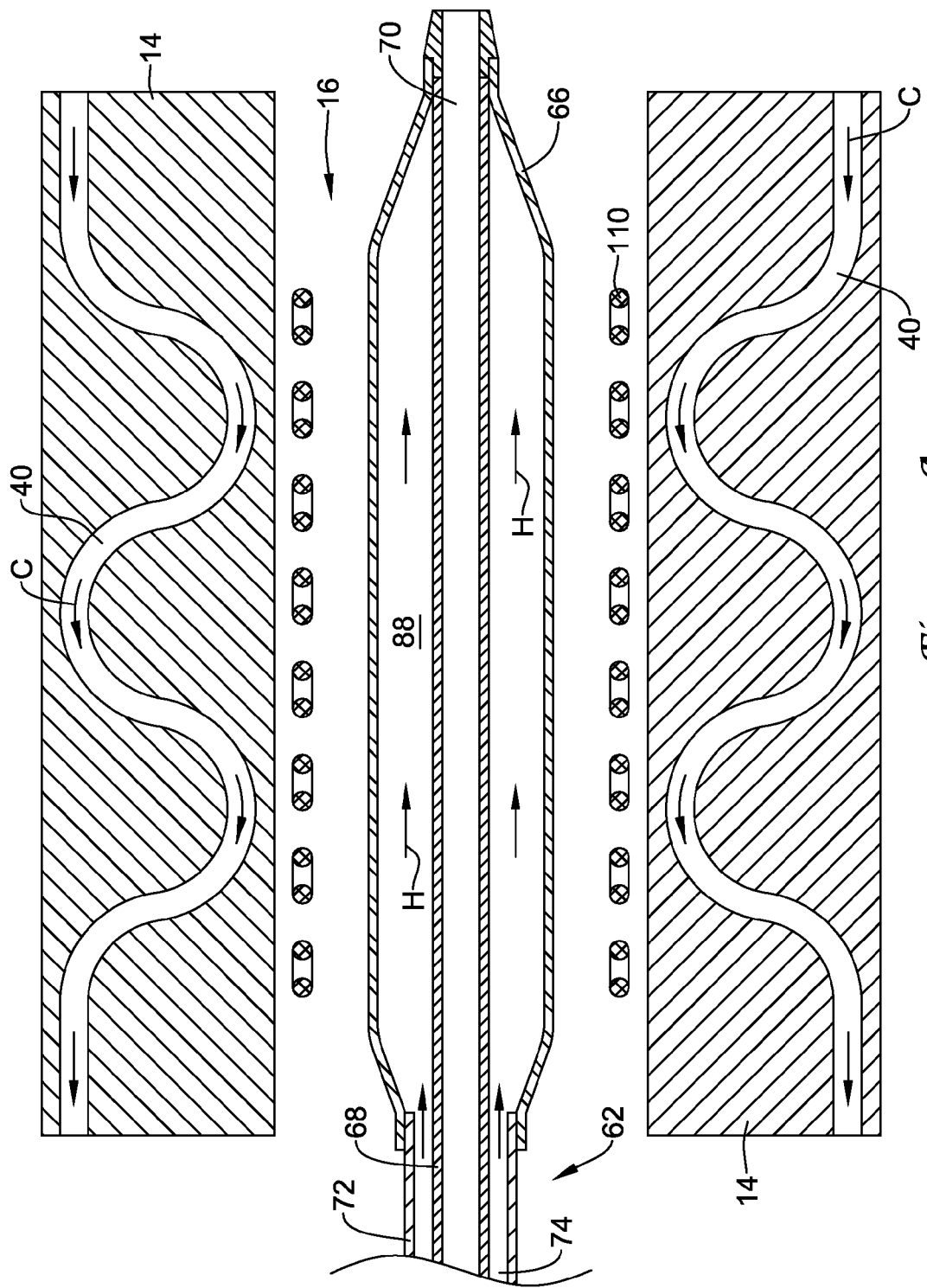
FIGS. 5A through 5C illustrate an exemplary crimping process in which a heated fluid is advanced through the inflation lumen and into the interior of the balloon to heat the balloon, and a fluid is passed through the crimping blades to cool the crimping elements.
Figure 5B:
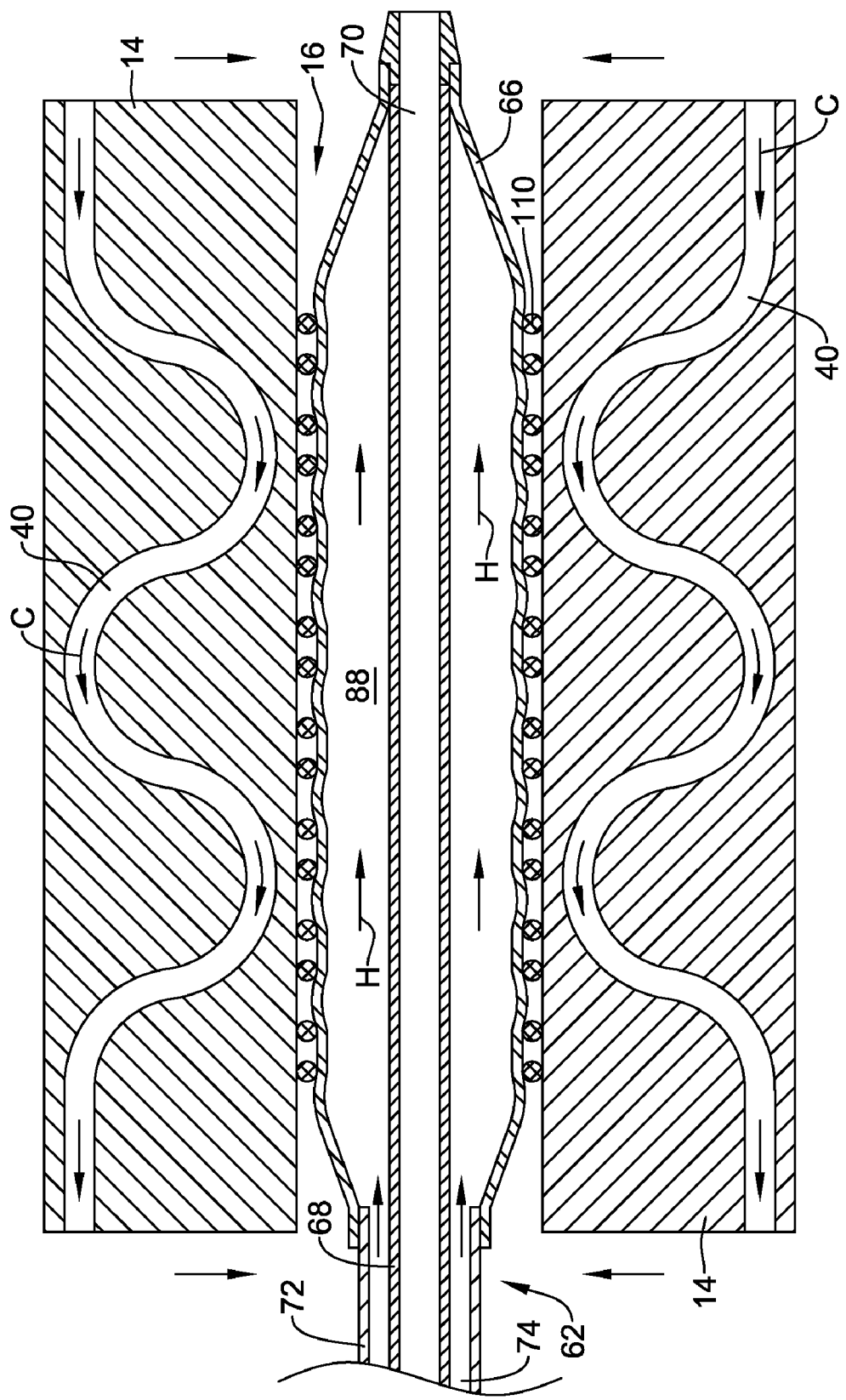
Figure 5C:
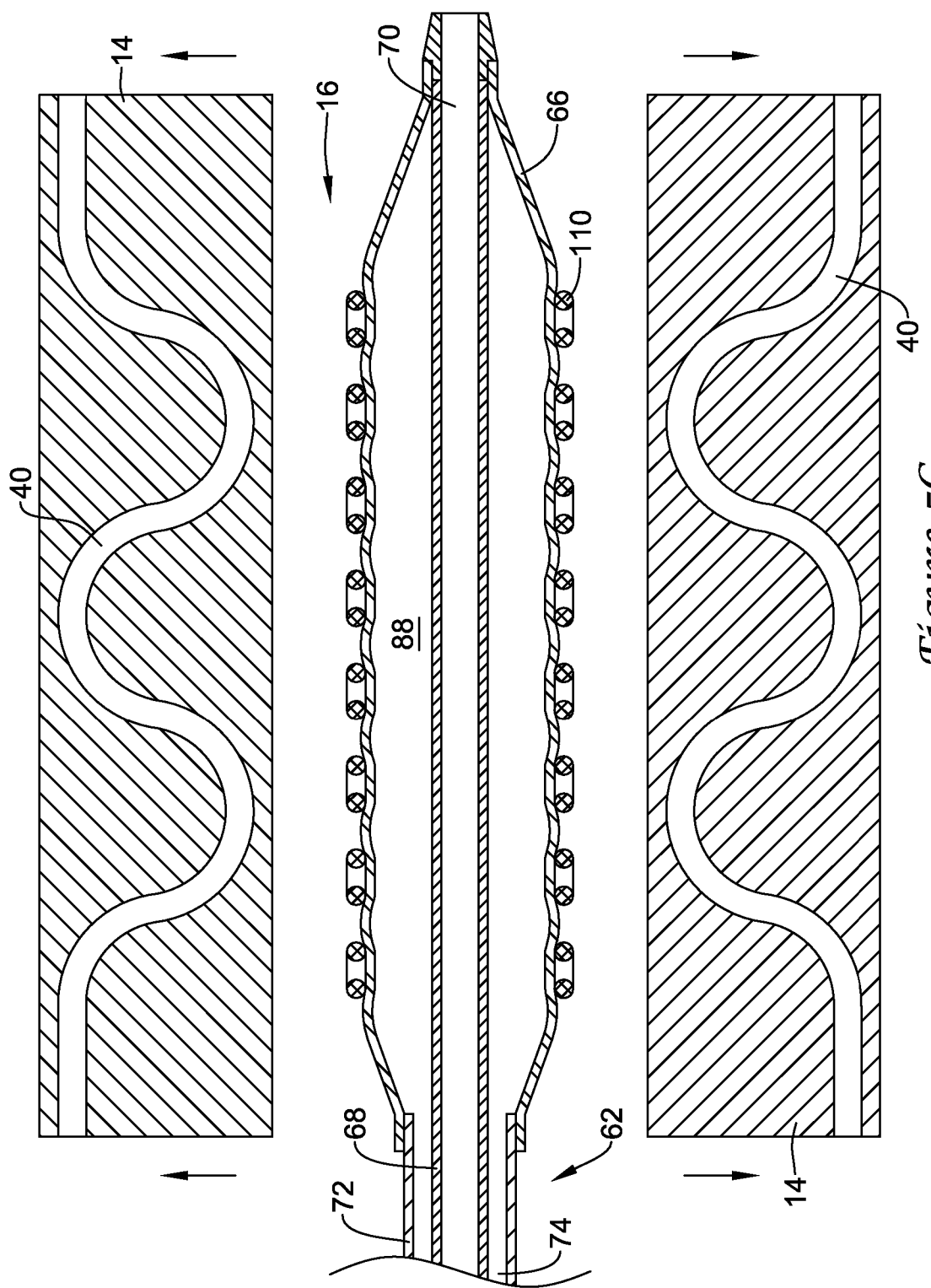

An exemplary crimping process for crimping a stent 110 onto the inflation balloon 66 of the balloon catheter 60 is illustrated in FIGS. 5A-5C. Some exemplary stents are disclosed in U.S. Pat. Nos. 6,730,117, 6,776,793, 6,945,993 and 6,981,986, of which the disclosures of each are each incorporated herein by reference.

The stent 110 may be a generally tubular member having an expandable framework including a plurality of interconnected segments defining interstitial spaces or openings therebetween (e.g., a fenestrated framework). The stent 110 may be expandable from a collapsed configuration (e.g., crimped onto the balloon 66 of the balloon catheter 60) to an expanded configuration (e.g., deployed within a vessel lumen of a patient).

The expandable framework of the stent 110 may be coated with a coating, such as a drug eluting coating, a protective coating, or other coating, prior to being loaded onto the balloon 66. Some exemplary coatings applied to a stent are disclosed in U.S. Pat. Nos. 6,099,563, 6,231,600, 6,569,195, 6,589,546, and 7,063,884, of which the disclosures of each are each incorporated herein by reference. In some embodiments, the coating may include a therapeutic agent which may be released, for example controllably released over a period of time, within a patient's body once the stent 110 is placed within the patient's body. In some embodiments, the stent 110 may be abluminally coated with the coating (i.e., coated on the radially outward surface of the stent 110). In other embodiments, the stent 110 may be conformally coated with the coating (i.e., coated on all surfaces of the stent 110).

As shown in FIG. 5A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 5A and 5B, a heating fluid H may be flowed through the inflation lumen 74 and into the interior 88 of the balloon 66. The heating fluid H may have a temperature greater than the glass transition temperature of the balloon material in order to sufficiently heat the balloon material. For instance, in some embodiments, the heating fluid H may have a temperature greater than 40° C., greater than 45° C., greater than 50° C., greater than 55° C., greater than 60° C., or greater than 70° C. Heat energy from the heating fluid H introduced into the interior 88 of the balloon 66 may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or a coating on the stent 110 to a temperature commensurate with the temperature of the balloon 66. For instance, raising the temperature of the stent 110 and/or the coating of the stent 110 to a temperature greater than 30° C. in some instances, or raising the temperature of the stent 110 and/or the coating of the stent 110 to a temperature greater than 40° C. in some instances, may adversely affect the performance and/or integrity of the stent 110 and/or the coating of the stent 110.

As such, the crimping apparatus 10 may be configured to maintain the temperature of the stent 110 and/or the coating of the stent 110 at a temperature less than 40° C. in some embodiments, or may maintain the temperature of the stent 110 and/or the coating of the stent 110 at a temperature less than 30° C. in some embodiments throughout the crimping process, even while the balloon material is heated to an elevated temperature greater than the temperature of the stent 110 and/or the coating of the stent 110.

During the crimping process, a cooling means or a cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 50° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 5B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 5B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 5B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 5B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 5C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the heating fluid H may be discontinued and/or the cooling fluid C may be discontinued. In some embodiments, however, it may be desired to continue to introduce the cooling fluid C through the crimping blades 14 as additional stents 110 are subsequently crimped to another balloon 66 of a balloon catheter 60 using the crimping apparatus 10. Thus, in such embodiments the crimping blades 14 may continuously be cooled by the cooling fluid C throughout multiple stent crimping cycles. Prior to crimping another stent 110 onto a balloon 66 of another balloon catheter 60, the heating source may be coupled to the next balloon catheter 60 to heat the balloon 66.

Figure 6A:
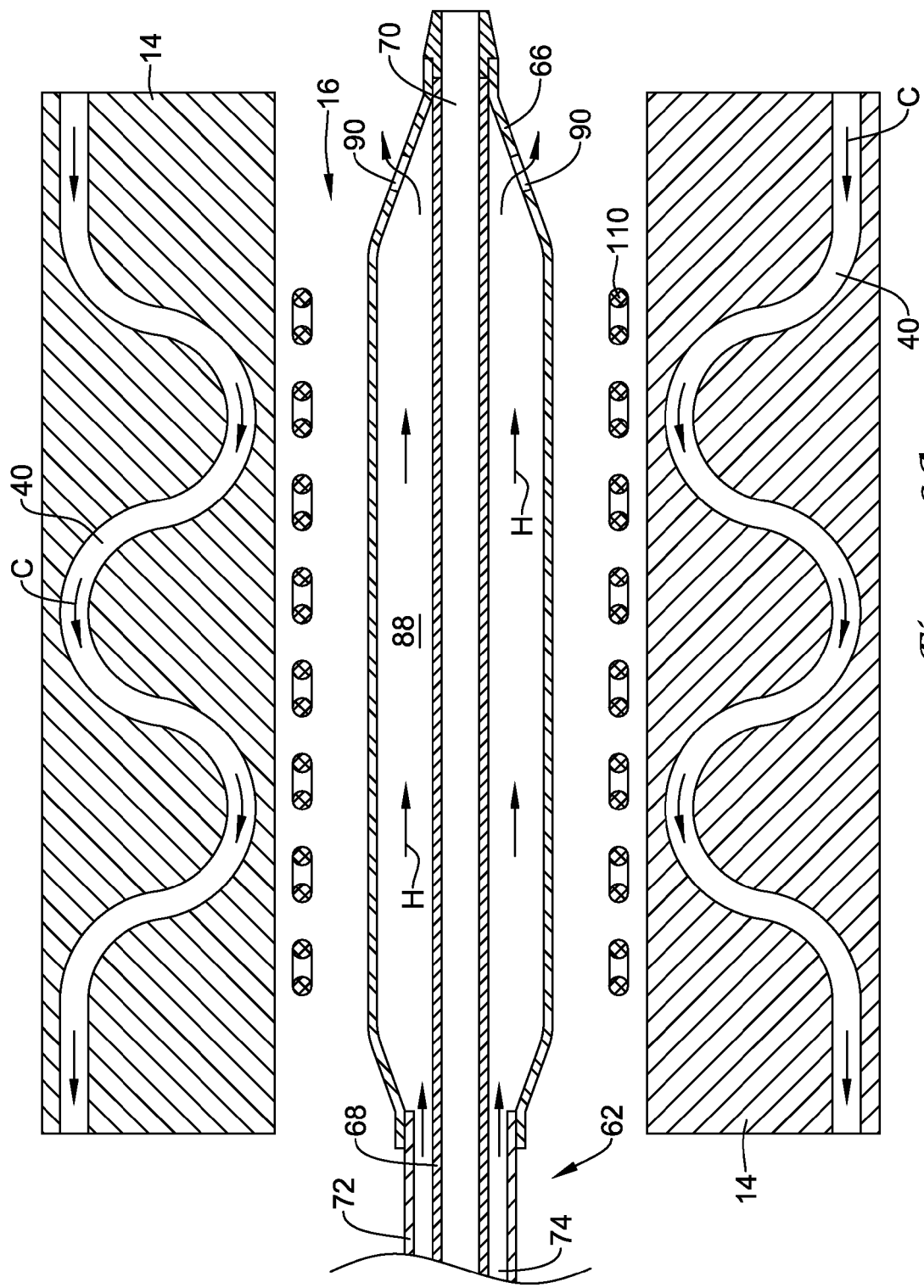
FIGS. 6A through 6C illustrate another exemplary crimping process in which a heated fluid is advanced through the inflation lumen, into the interior of the balloon and out an opening in the balloon to heat the balloon, and a fluid is passed through the crimping blades to cool the crimping elements.
Figure 6B:
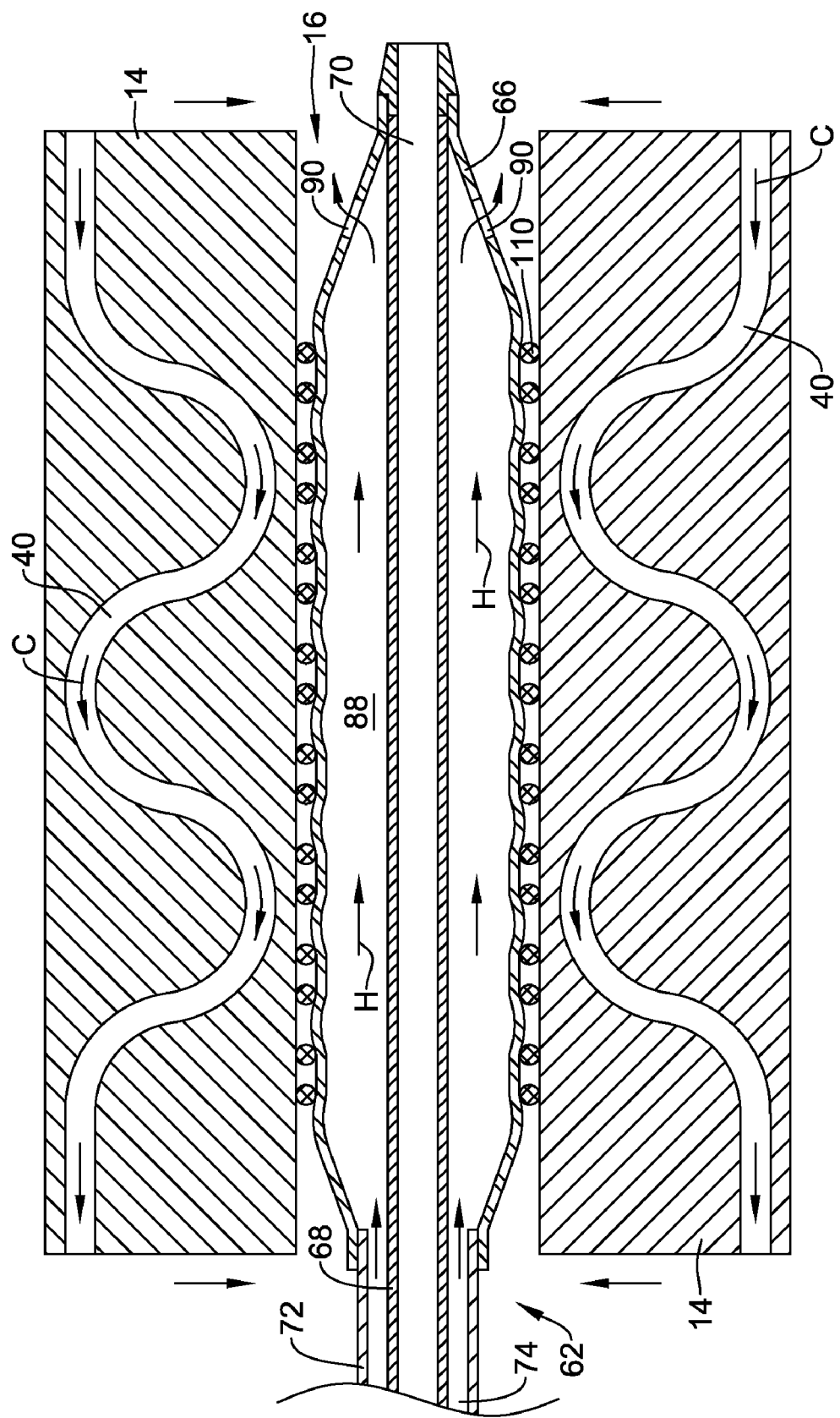
Figure 6C:
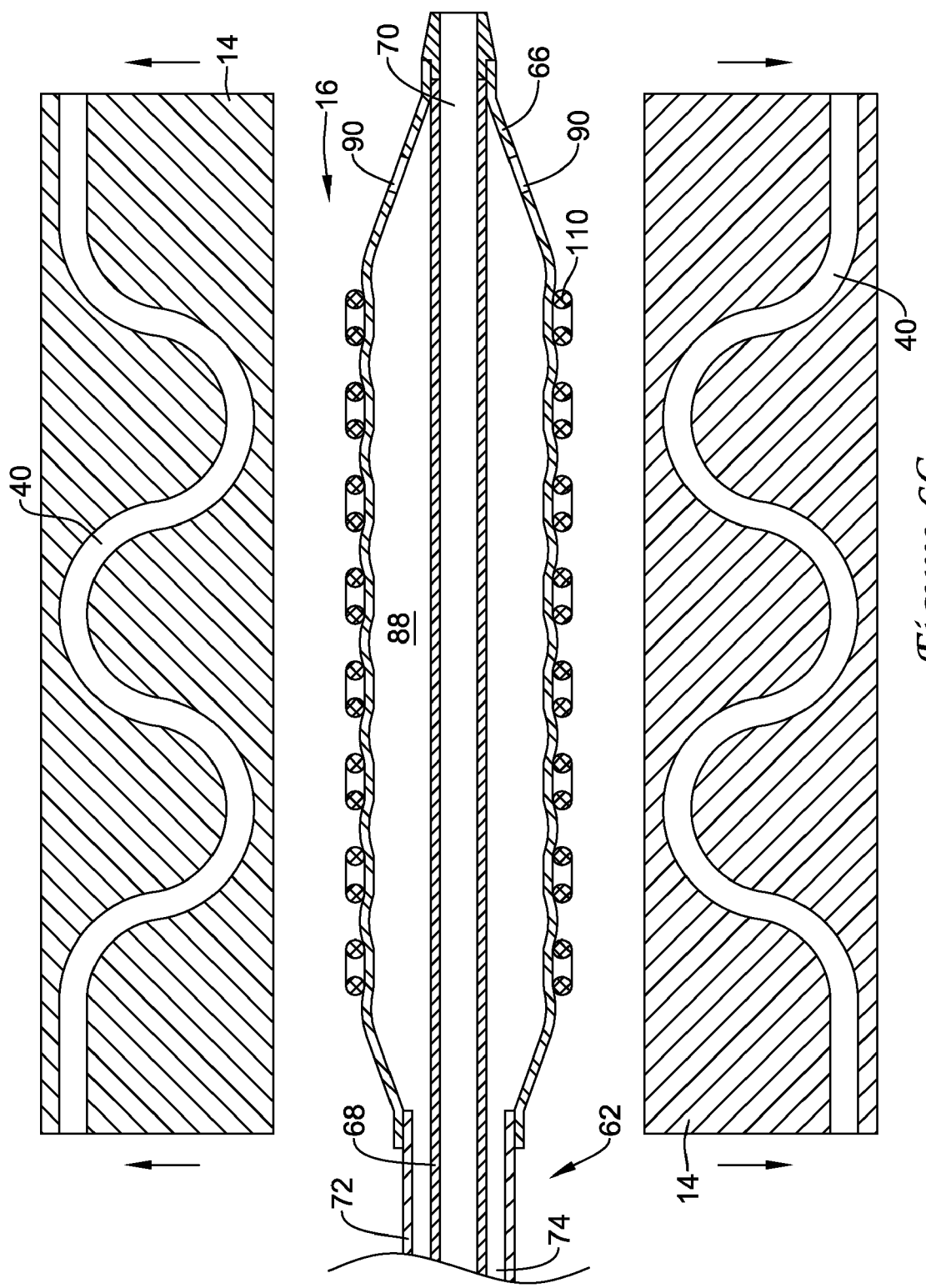

Another exemplary crimping process for crimping a stent 110 onto the inflation balloon 66 of the balloon catheter 60 is illustrated in FIGS. 6A-6C. Similar to that discussed above, the stent 110 may be any desired stent and may include a coating (e.g., a drug eluting coating, a protective coating, etc.), such as an abluminal coating or a conformal coating.

As shown in FIG. 6A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 6A and 6B, a heating fluid H may be flowed through the inflation lumen 74 and into the interior 88 of the balloon 66. The balloon 66 may include one or more openings 90 allowing the heating fluid H to then exit the balloon 66 as the heating fluid H flows through the balloon 66. Thus, the interior 88 of the balloon 66 may be subjected to a continuous flow of the heating fluid H flowing into the interior 88 of the balloon 66 through the inflation lumen 74 and flowing out of the interior 88 of the balloon 66 through the openings 90. In some embodiments, the heating fluid H flowing out of the openings 90 may be collected and recirculated through the balloon 66, and/or used in a subsequent crimping process of another stent 110. The heating fluid H may have a temperature greater than the glass transition temperature of the balloon material in order to sufficiently heat the balloon material. For instance, in some embodiments, the heating fluid H may have a temperature greater than 40° C., greater than 45° C., greater than 50° C., greater than 55° C., greater than 60° C., or greater than 70° C. Heat energy from the heating fluid H introduced into the interior 88 of the balloon 66 may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or the coating on the stent 110 to a temperature commensurate with the temperature of the balloon 66. For instance, raising the temperature of the stent 110 and/or the coating of the stent 110 to a temperature greater than 30° C. in some instances, or raising the temperature of the stent 110 and/or the coating of the stent 110 to a temperature greater than 40° C. in some instances, may adversely affect the performance and/or integrity of the stent and/or the coating of the stent 110.

As such, the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

During the crimping process, a cooling means or cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 50° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 6B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 6B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 6B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 6B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with the stent 110 (direct or indirect contact) to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 6C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the heating fluid H may be discontinued and/or the cooling fluid C may be discontinued. In some embodiments, however, it may be desired to continue to introduce the cooling fluid C through the crimping blades 14 as additional stents 110 are subsequently crimped to a balloon 66 of a balloon catheter 60 using the crimping apparatus 10. Thus, in such embodiments the crimping blades 14 may continuously be cooled by the fluid C throughout multiple stent crimping cycles. Prior to crimping another stent 110 onto a balloon 66 of another balloon catheter 60, the heating source may be coupled to the next balloon catheter 60 to heat the balloon 66.

Subsequent to crimping the stent 110 onto the balloon 66 of the balloon catheter 60, the openings 90 in the balloon 66 may be filled, covered, sealed or otherwise closed. For instance, in some embodiments the openings 90 may be thermally sealed with a laser, or the openings 90 may be adhesively sealed after the crimping process has been performed.

Figure 7A:
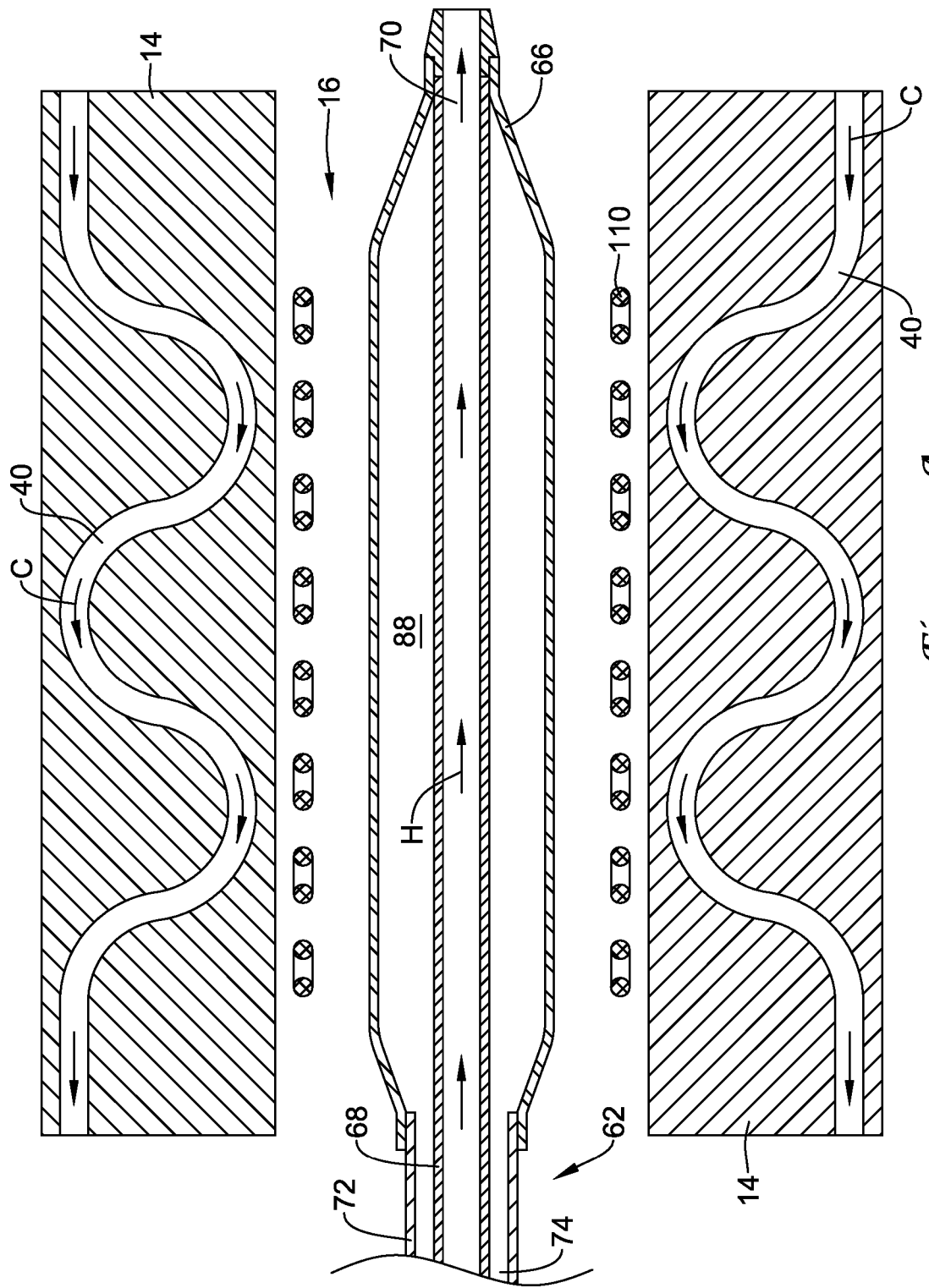
FIGS. 7A through 7C illustrate another exemplary crimping process in which a heated fluid is advanced through the guidewire lumen to heat the balloon, and a fluid is passed through the crimping blades to cool the crimping elements.
Figure 7B:
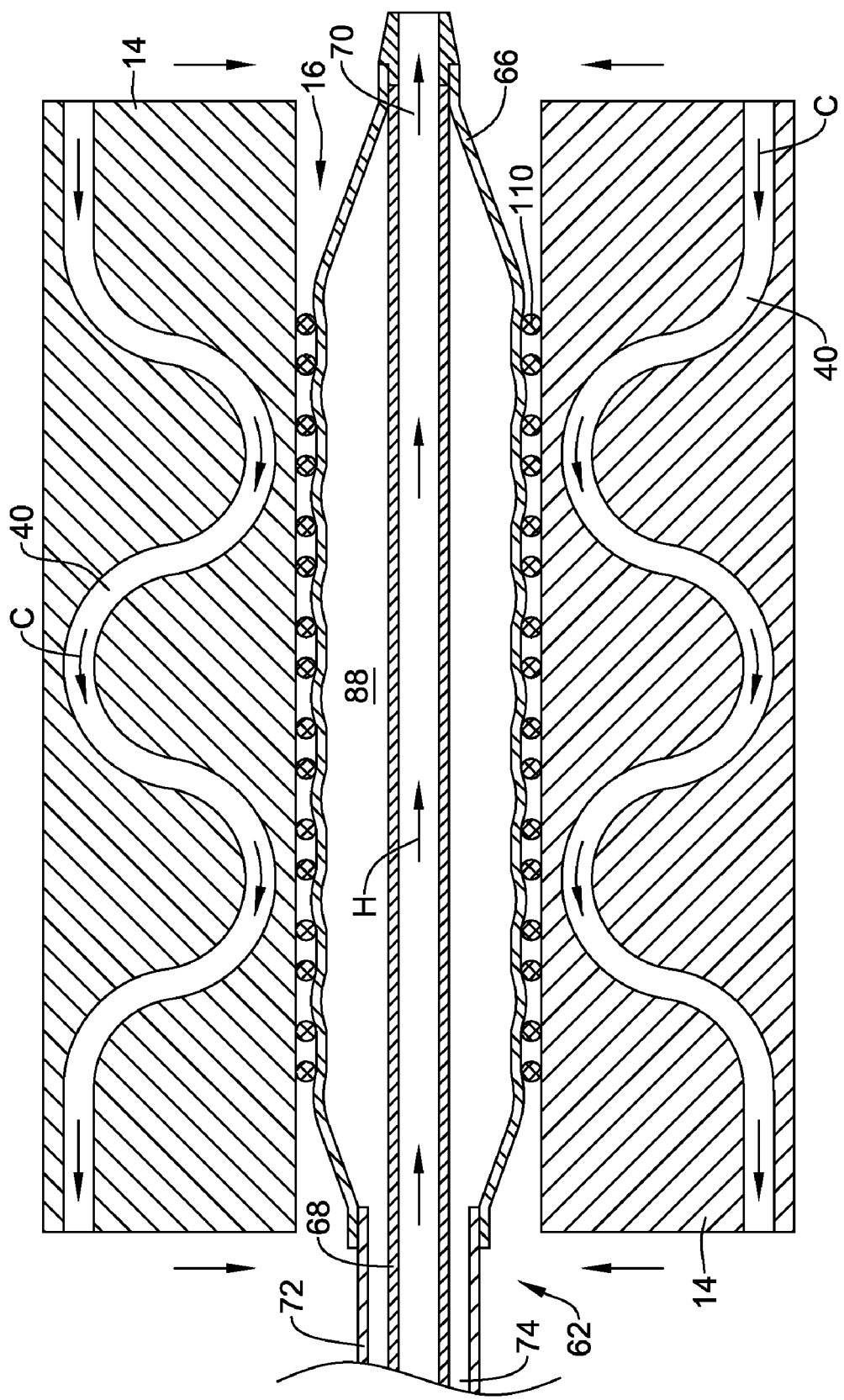
Figure 7C:
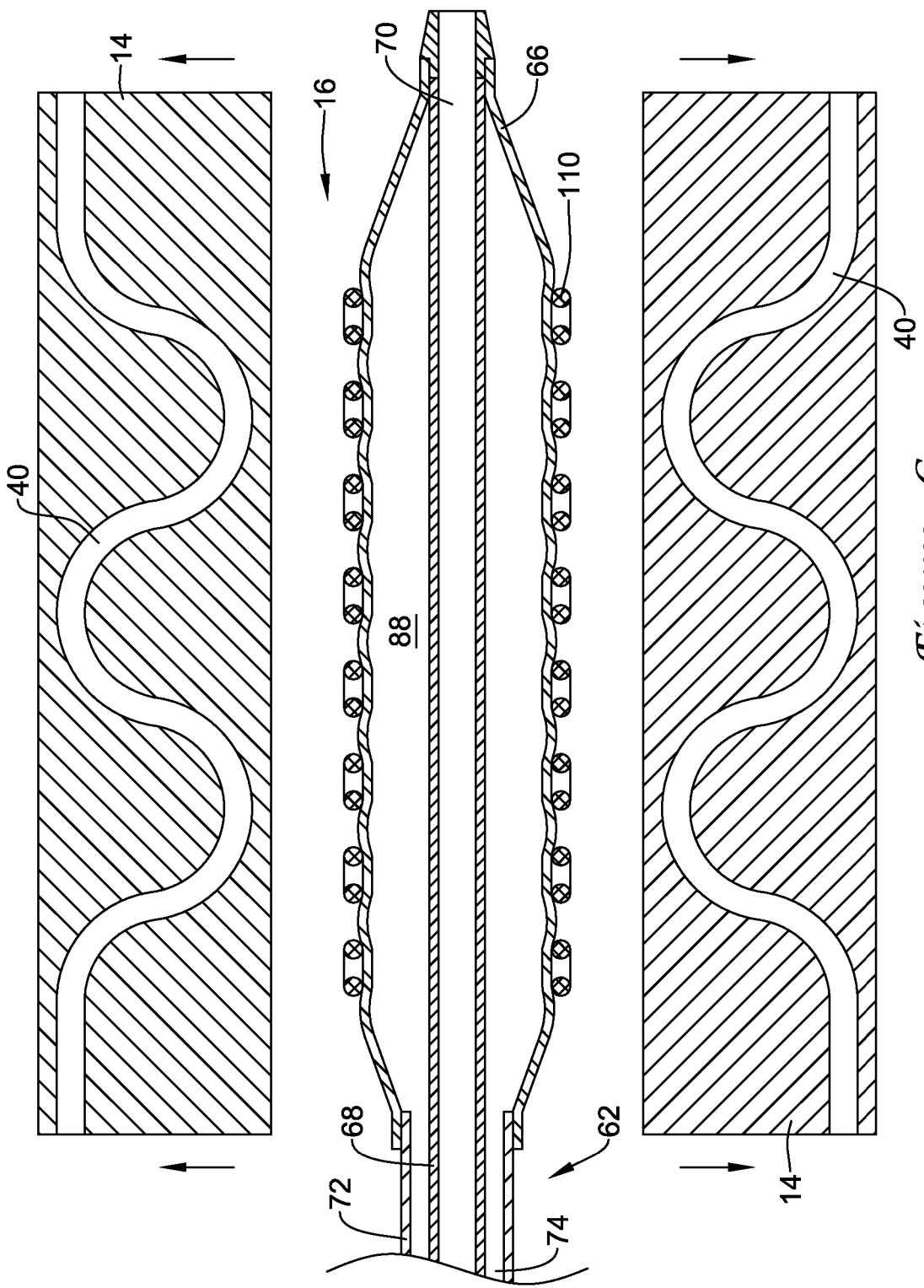

Another exemplary crimping process for crimping a stent 110 onto the inflation balloon 66 of the balloon catheter 60 is illustrated in FIGS. 7A-7C. Similar to that discussed above, the stent 110 may be any desired stent and may include a coating (e.g., a drug eluting coating, a protective coating, etc.), such as an abluminal coating or a conformal coating.

As shown in FIG. 7A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 7A and 7B, a heating fluid H may be flowed through the guidewire lumen 70 of the balloon catheter 60. Thus, the guidewire lumen 70 may be subjected to a continuous flow of the heating fluid H flowing through the guidewire lumen 70 from a heating source proximal of the balloon 66 to the distal guidewire port distal of the balloon 66. Therefore, the heating fluid H may pass through the guidewire lumen 70 interior of the balloon 66. In some embodiments, the heating fluid H may be collected as it exits the distal end of the catheter, and may be recirculated through the guidewire lumen 70 during the crimping process and/or used while crimping another stent 110 to another balloon catheter 60 during another crimping process. The heating fluid H may have a temperature greater than the glass transition temperature of the balloon material in order to sufficiently heat the balloon material. For instance, in some embodiments, the heating fluid H may have a temperature greater than 40° C., greater than 45° C., greater than 50° C., greater than 55° C., greater than 60° C., or greater than 70° C. Heat energy from the heating fluid H introduced through the guidewire lumen 70 may be transferred to other components of the balloon catheter 60 and transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or coating on the stent 110 to a temperature commensurate with the temperature of the balloon 66. For instance, raising the temperature of the stent 110 and/or coating of the stent 110 to a temperature greater than 30° C. in some instances, or raising the temperature of the stent 110 and/or coating of the stent 110 to a temperature greater than 40° C. in some instances, may adversely affect the performance and/or integrity of the stent 110 and/or coating of the stent 110.

As such, the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

During the crimping process, a cooling means or cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 5° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 7B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 7B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 7B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 7B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 7C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the heating fluid H may be discontinued and/or the cooling fluid C may be discontinued. In some embodiments, however, it may be desired to continue to introduce the cooling fluid C through the crimping blades 14 as additional stents 110 are subsequently crimped to a balloon 66 of a balloon catheter 60 using the crimping apparatus 10. Thus, in such embodiments the crimping blades 14 may continuously be cooled by the fluid C throughout multiple stent crimping cycles. Prior to crimping another stent 110 onto a balloon 66 of another balloon catheter 60, the heating source may be coupled to the balloon catheter 60 to heat the balloon 66.

Figure 8A:
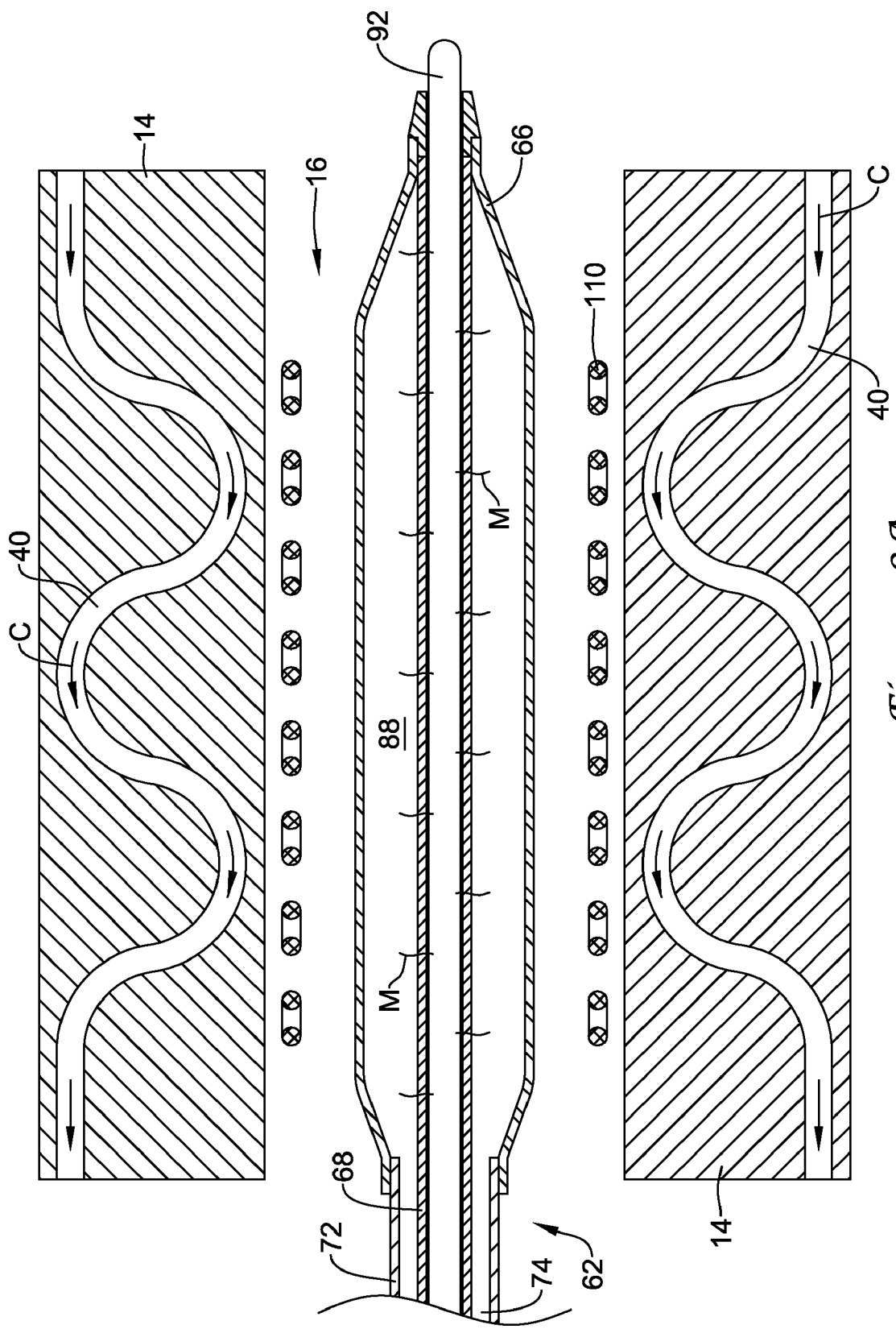
FIGS. 8A through 8C illustrate another exemplary crimping process in which a heated mandrel is positioned in the guidewire lumen to heat the balloon, and a fluid is passed through the crimping blades to cool the crimping elements.
Figure 8B:
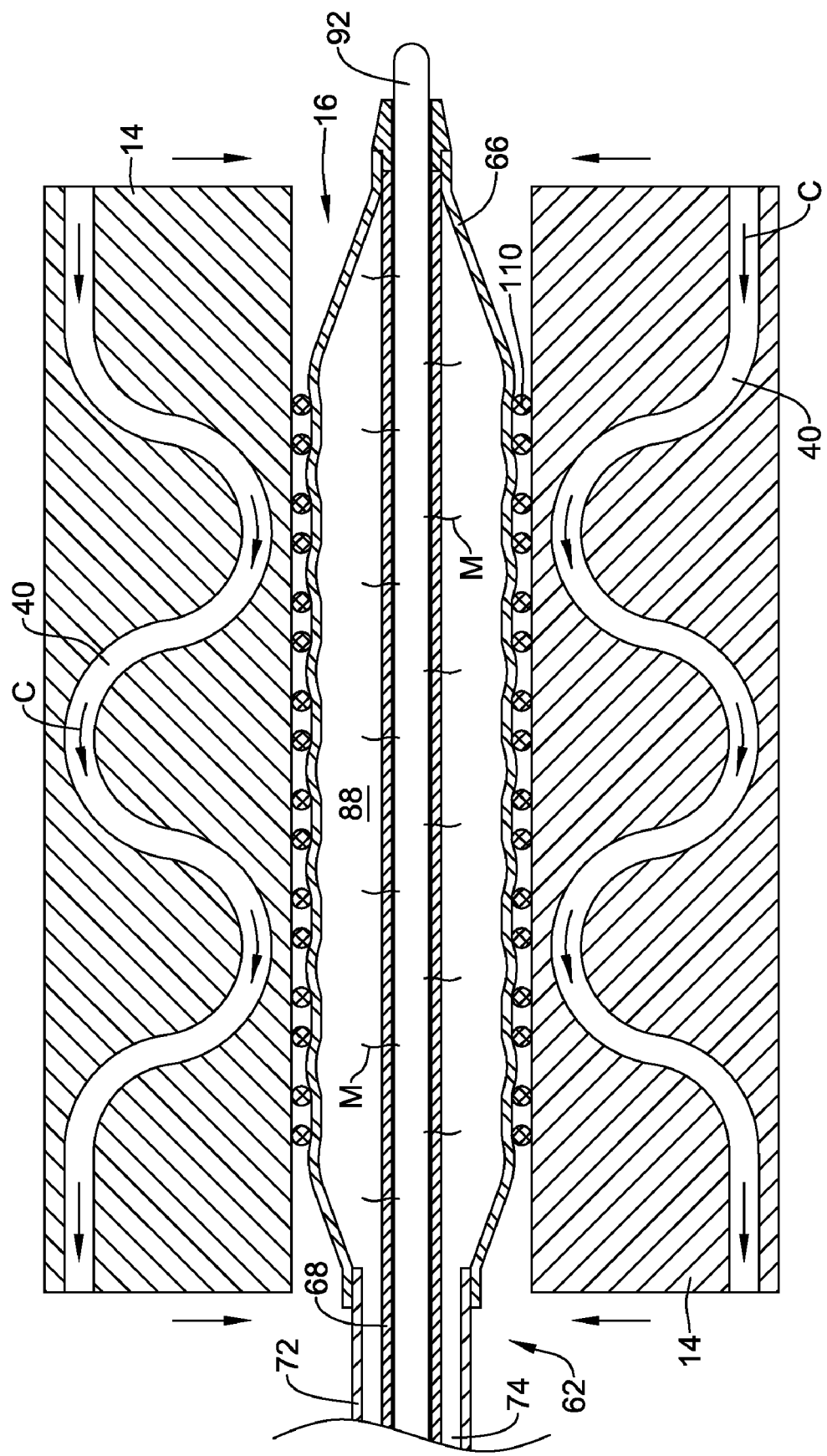
Figure 8C:
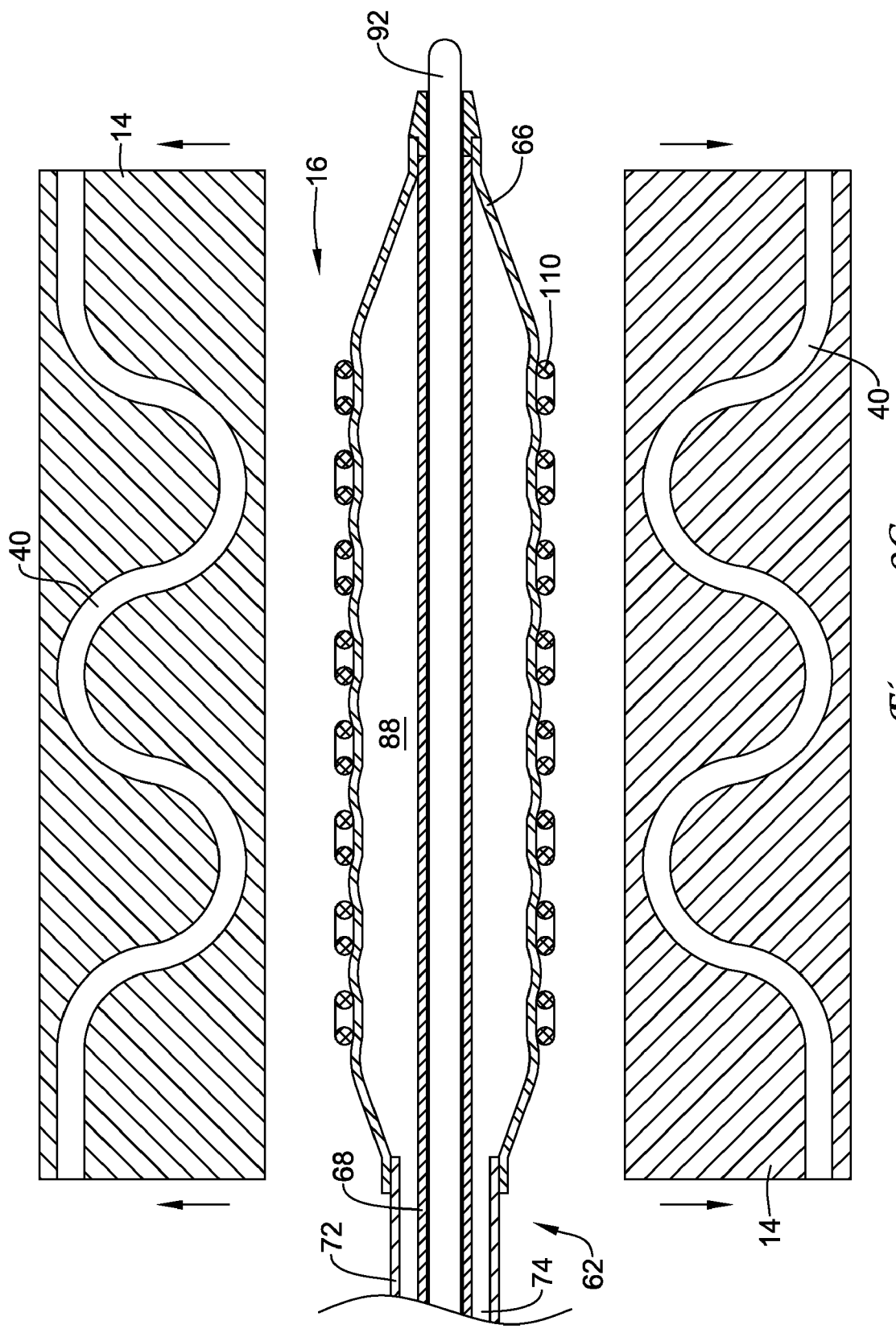

Another exemplary crimping process for crimping a stent 110 onto the inflation balloon 66 of the balloon catheter 60 is illustrated in FIGS. 8A-8C. Similar to that discussed above, the stent 110 may be any desired stent and may include a coating (e.g., a drug eluting coating, a protective coating, etc.), such as an abluminal coating or a conformal coating.

As shown in FIG. 8A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 8A and 8B, a heating mandrel 92 may be positioned within the guidewire lumen 70 of the elongate shaft 62 of the catheter 60 such that the heating mandrel 92 is located radially interior of the balloon 66. The heating mandrel 92 may dissipate heat energy M to heat the balloon 66. For example, in some embodiments, an electrical current may be passed through the heating mandrel 92 to generate heat energy M from resistive heating of the heating mandrel 92. In other embodiments, the heating mandrel 92, which may include a ferromagnetic material, may be subjected to an alternating magnetic field to generate heat energy M through a hysteresis effect. In yet other embodiments, the heating mandrel 92 may be heated by conduction heating, permitting heat energy M to dissipate from the mandrel 92. The heating mandrel 92 may have a temperature greater than the glass transition temperature of the balloon material in order to sufficiently heat the balloon material. For instance, in some embodiments, the heating mandrel 92 may have a temperature greater than 40° C., greater than 45° C., greater than 50° C., greater than 55° C., greater than 60° C., or greater than 70° C. Heat energy M dissipating from the heating mandrel 92 may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or coating on the stent 110 to a temperature commensurate with the temperature of the balloon 66. For instance, raising the temperature of the stent 110 and/or coating of the stent 110 to a temperature greater than 30° C. in some instances, or raising the temperature of the stent 110 and/or coating of the stent 110 to a temperature greater than 40° C. in some instances, may adversely affect the performance and/or integrity of the stent 110 and/or coating of the stent 110.

As such, the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

During the crimping process, a cooling means or cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 5° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 8B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 8B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 8B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 8B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 8C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the heat energy M dissipating from the heating mandrel 92 may be discontinued and/or the heating mandrel 92 may be removed from the guidewire lumen 70, and/or the cooling fluid C may be discontinued. In some embodiments, however, it may be desired to continue to introduce the cooling fluid C through the crimping blades 14 as additional stents 110 are subsequently crimped to a balloon 66 of a balloon catheter 60 using the crimping apparatus 10. Thus, in such embodiments the crimping blades 14 may continuously be cooled by the fluid C throughout multiple stent crimping cycles. Prior to crimping another stent 110 onto a balloon 66 of another balloon catheter 60, the heating mandrel 92 may be inserted into the guidewire lumen 70 of the next balloon catheter 60 to heat the balloon 66.

Figure 9A:
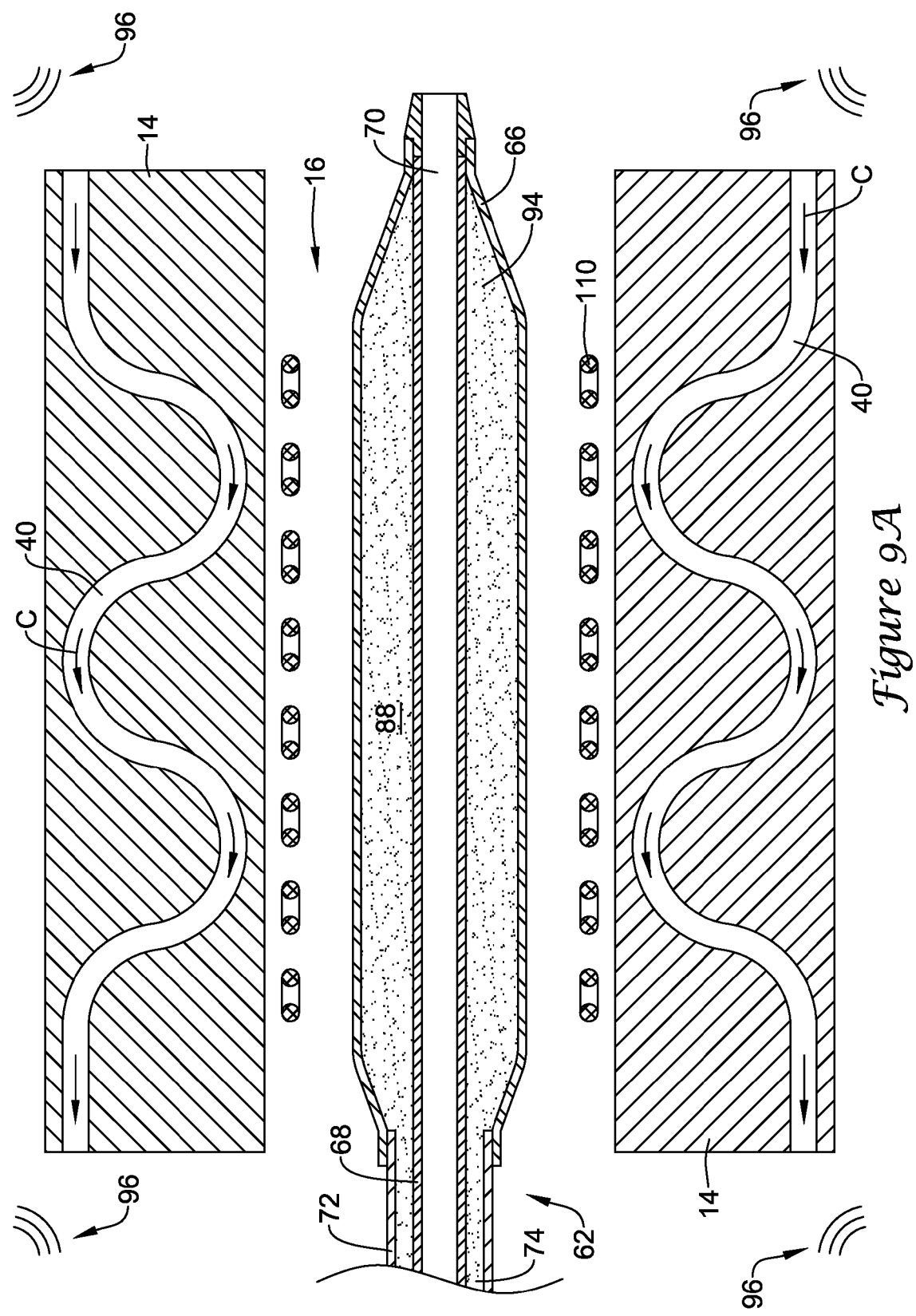
FIGS. 9A through 9C illustrate another exemplary crimping process in which a moisture rich environment provided in the interior of the balloon is subjected to electromagnetic waves to heat the balloon, and a fluid is passed through the crimping blades to cool the crimping elements.
Figure 9B:
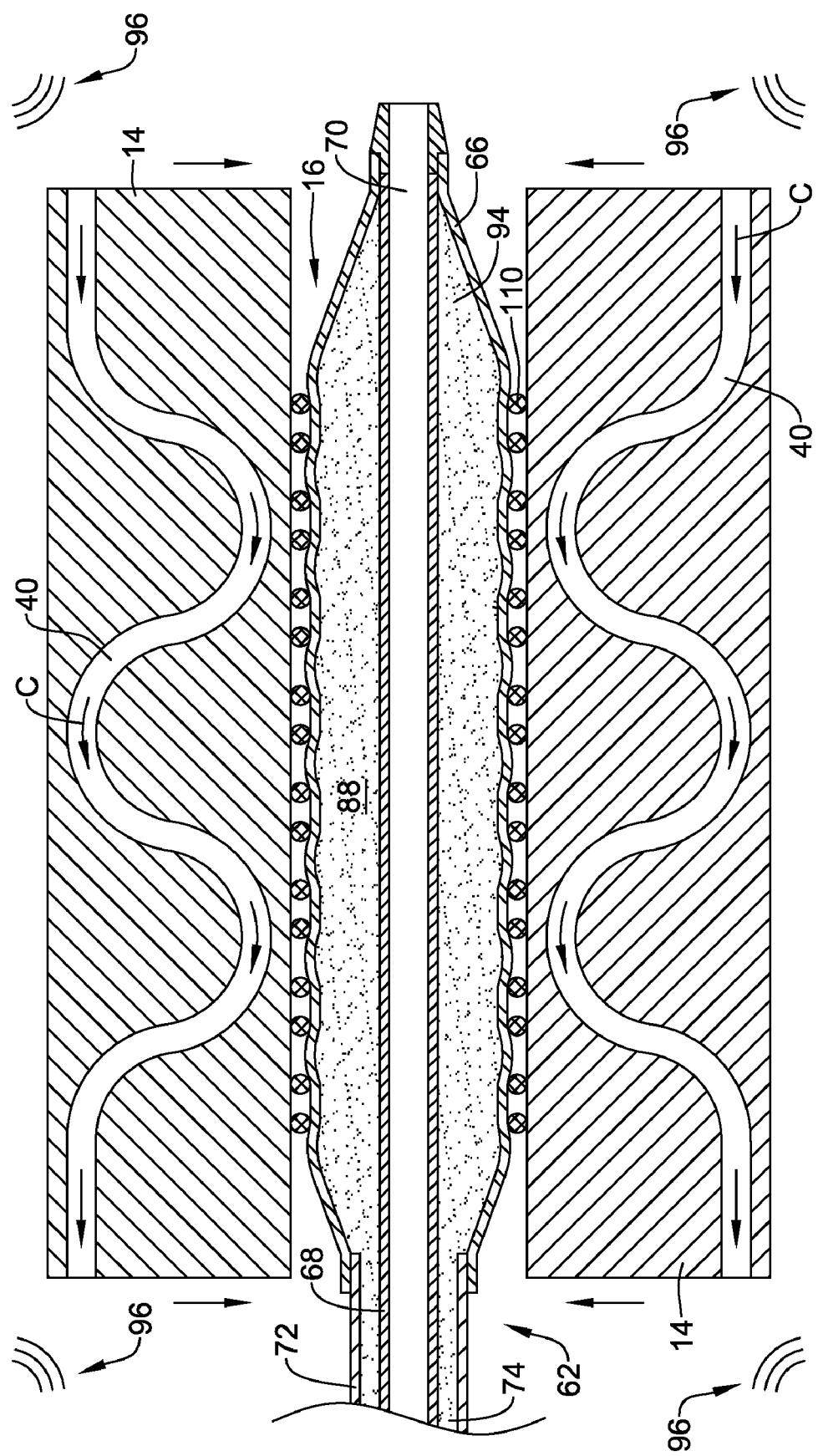
Figure 9C:
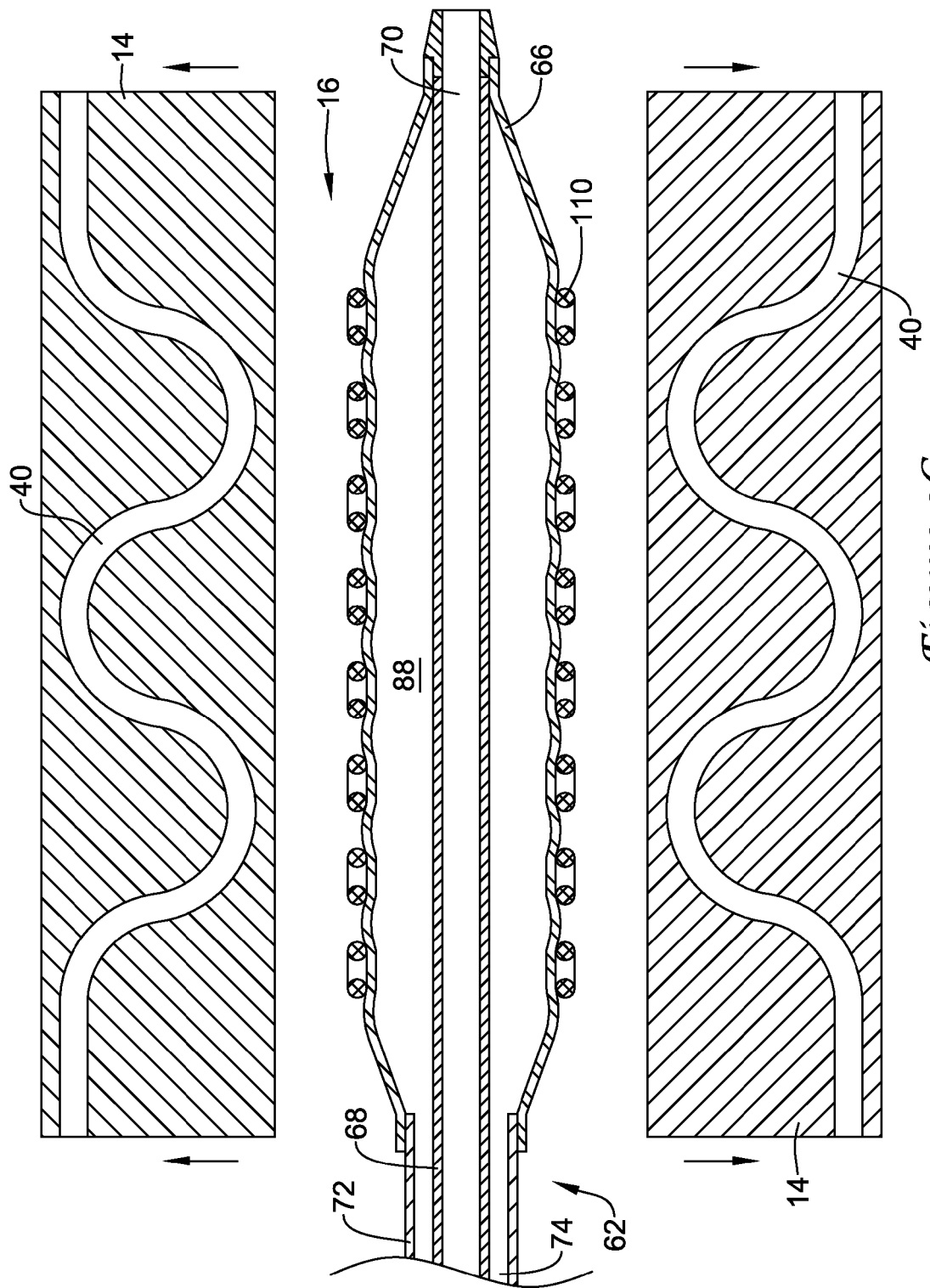

Another exemplary crimping process for crimping a stent 110 onto the inflation balloon 66 of the balloon catheter 60 is illustrated in FIGS. 9A-9C. Similar to that discussed above, the stent 110 may be any desired stent and may include a coating (e.g., a drug eluting coating, a protective coating, etc.), such as an abluminal coating or a conformal coating.

As shown in FIG. 9A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 9A and 9B, a moisture rich environment 94 may be flowed through the inflation lumen 74 and into the interior 88 of the balloon 66. In some embodiments, the moisture rich environment 94 may be air or other gas including suspended water vapor, for instance high humidity air having a relative humidity of 70% or greater, 80% or greater, 90% or greater, or 95% or greater. Thus, in some embodiments the interior 88 of the balloon 66 may be filled with a gas, such as air, having a high concentration of suspended water vapor. It is noted that in other embodiments, the moisture rich environment 94 may be introduced within the guidewire lumen 70.

During the crimping process, the moisture rich environment 94 within the interior 88 of the balloon 66 may be subjected to electromagnetic wave energy 96, such as microwave energy. In some embodiments, the electromagnetic energy 96 may have a frequency in the range of between about 300 MHz to about 300 GHz, in the range of between about 900 MHz to about 3000 MHz, in the range of about 915 MHz, or in the range of about 2450 MHz. In some embodiments the crimping apparatus 10 may be positioned in an enclosure which resonates the microwave energy 96 toward the balloon 66 of the balloon catheter 60. In some embodiments, a Faraday cage may be used to prevent the electromagnetic waves 96 from escaping into the environment.

Moisture (e.g., water vapor) in the moisture rich environment 94 may absorb energy from the electromagnetic waves 96 through dielectric heating. Water is an electric dipole, having a positive charge at one end and a negative charge at the other. The water molecules, or molecules of another electric dipole, in the moisture rich environment 94, continuously oscillate or rotate to align with the alternating electric field induced by the electromagnetic waves 96. The oscillating molecular movement of the water molecules, or molecules of another electric dipole, generate heat energy.

In some embodiments, the moisture rich environment 94 may reach a temperature greater than the glass transition temperature of the balloon material in order to sufficiently heat the balloon material. For instance, in some embodiments, the moisture rich environment 94 may reach a temperature greater than 40° C., greater than 45° C., greater than 50° C., greater than 55° C., greater than 60° C., or greater than 70° C. Heat energy generated by the electromagnetic waves 96 inducing alternating movement of the water molecules may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or coating on the stent 110 to a temperature commensurate with the temperature of the balloon 66. For instance, raising the temperature of the stent 110 and/or coating of the stent 110 to a temperature greater than 30° C. in some instances, or raising the temperature of the stent 110 and/or coating of the stent 110 to a temperature greater than 40° C. in some instances, may adversely affect the performance and/or integrity of the stent 110 and/or coating of the stent 110.

As such, the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

During the crimping process, a cooling means or cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 5° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 9B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 9B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 9B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 9B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 9C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the electromagnetic energy 96 may be discontinued and/or the cooling fluid C may be discontinued. In some embodiments, a vacuum may be drawn through the inflation lumen 74 to draw the moisture rich environment 94 from the interior 88 of the balloon 66. In some embodiments, it may be desired to continue to introduce the cooling fluid C through the crimping blades 14 as additional stents 110 are subsequently crimped to a balloon 66 of a balloon catheter 60 using the crimping apparatus 10. Thus, in such embodiments the crimping blades 14 may continuously be cooled by the fluid C throughout multiple stent crimping cycles. Prior to crimping another stent 110 onto a balloon 66 of another balloon catheter 60, the electromagnetic energy 96 may be propagated toward the next balloon catheter 60 to heat the balloon 66.

Figure 10A:
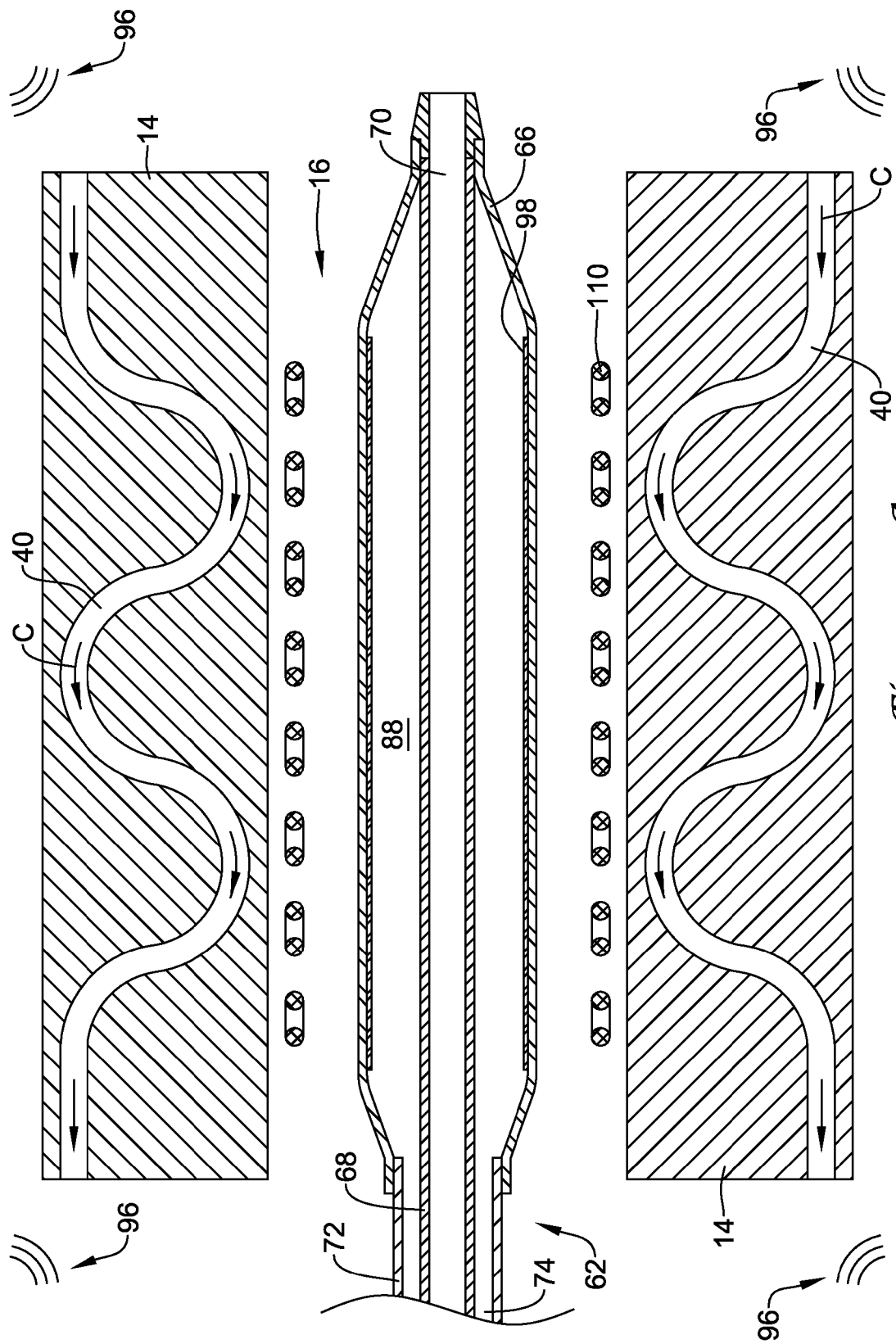
FIGS. 10A through 10C illustrate another exemplary crimping process in which a moisture rich layer within the interior of the balloon is subjected to electromagnetic waves to heat the balloon, and a fluid is passed through the crimping blades to cool the crimping elements.
Figure 10B:
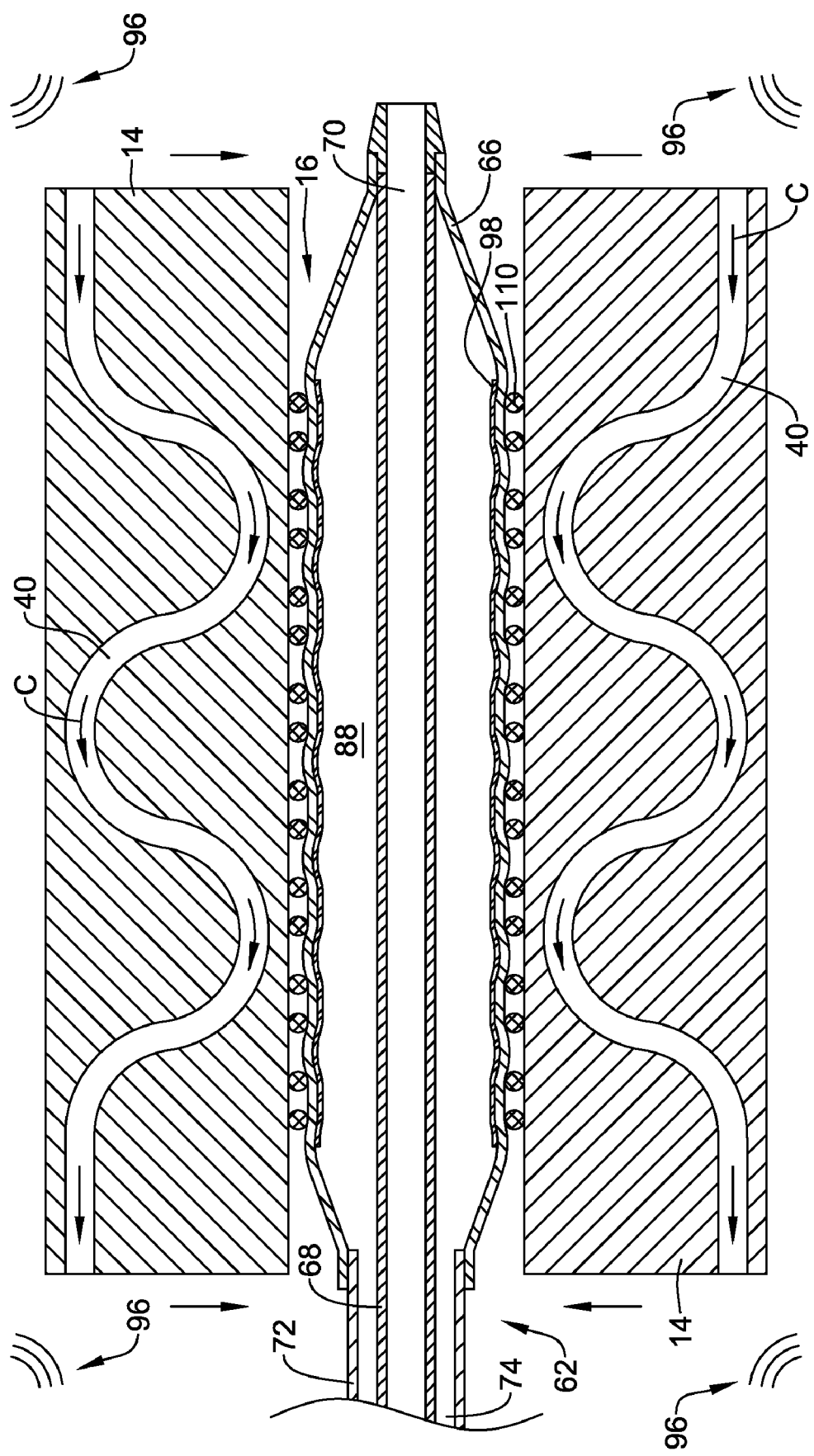
Figure 10C:
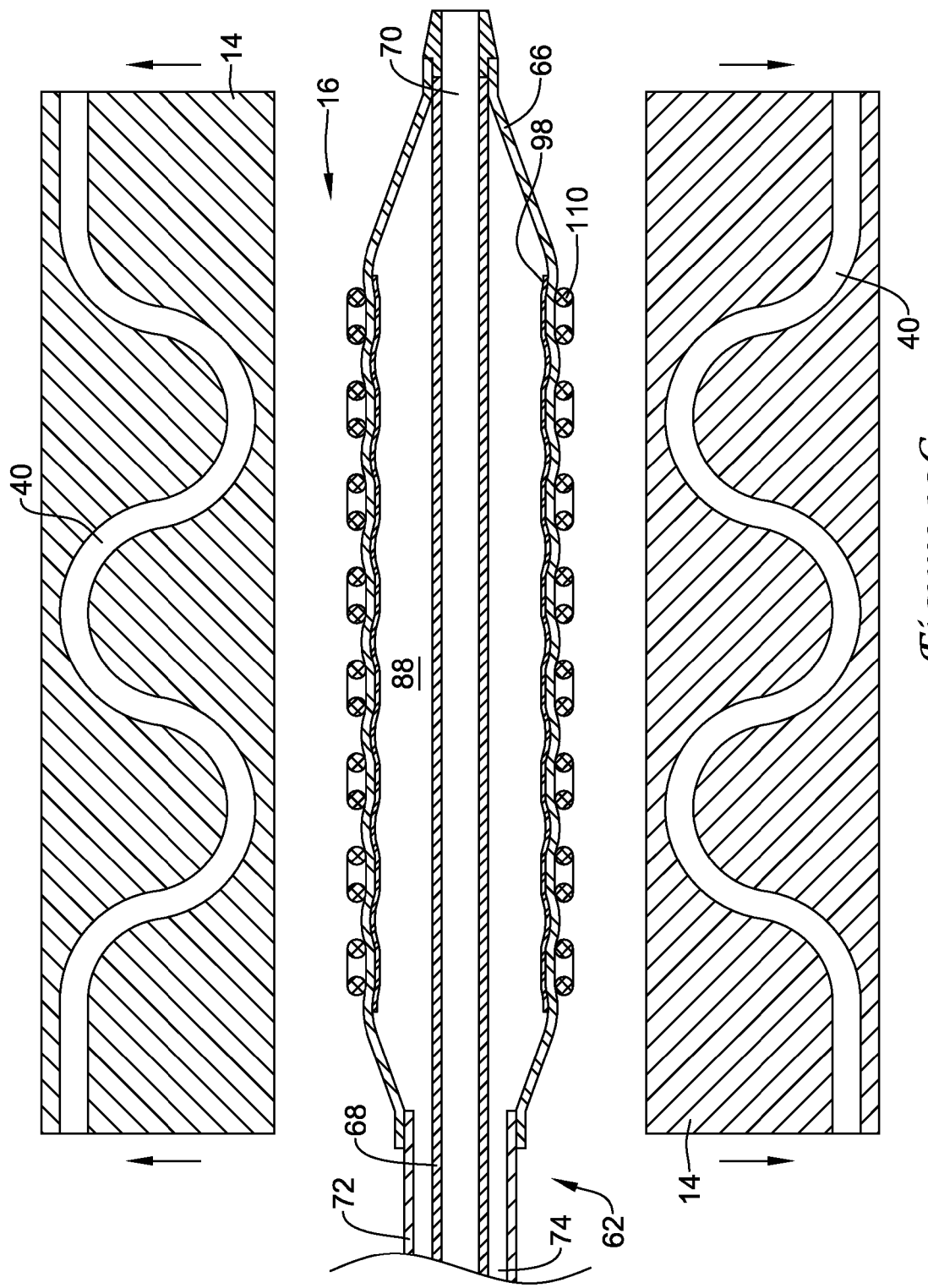

Another exemplary crimping process for crimping a stent 110 onto the inflation balloon 66 of the balloon catheter 60 is illustrated in FIGS. 10A-10C. Similar to that discussed above, the stent 110 may be any desired stent and may include a coating (e.g., a drug eluting coating, a protective coating, etc.), such as an abluminal coating or a conformal coating.

As shown in FIG. 10A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 10A and 10B, a moisture rich layer 98, or other layer which is responsive to electromagnetic energy, may be located within the interior 88 of the balloon 66. For example, the moisture rich layer 98 may be located on an inner surface of the material of the balloon 66 facing the interior 88 of the balloon 66.

During the crimping process, the moisture rich layer 98 within the interior 88 of the balloon 66 may be subjected to electromagnetic wave energy 96, such as microwave energy. In some embodiments, the electromagnetic energy 96 may have a frequency in the range of between about 300 MHz to about 300 GHz, in the range of between about 900 MHz to about 3000 MHz, in the range of about 915 MHz, or in the range of about 2450 MHz. In some embodiments the crimping apparatus 10 may be positioned in an enclosure which resonates the microwave energy 96 toward the balloon 66 of the balloon catheter 60. In some embodiments, a Faraday cage may be used to prevent the electromagnetic waves 96 from escaping into the environment.

Moisture (e.g., water vapor) in the moisture rich layer 98 may absorb energy from the electromagnetic waves 96 through dielectric heating. Water is an electric dipole, having a positive charge at one end and a negative charge at the other. The water molecules, or molecules of another electric dipole, in the moisture rich layer 98, continuously oscillate or rotate to align with the alternating electric field induced by the electromagnetic waves 96. The oscillating molecular movement of the water molecules, or molecules of another electric dipole, generate heat energy.

In some embodiments, the moisture rich layer 98 may reach a temperature greater than the glass transition temperature of the balloon material in order to sufficiently heat the balloon material. For instance, in some embodiments, the moisture rich layer 98 may reach a temperature greater than 40° C., greater than 45° C., greater than 50° C., greater than 55° C., greater than 60° C., or greater than 70° C. Heat energy generated by the electromagnetic waves 96 inducing alternating movement of the water molecules may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

Although it may be desirable to heat the balloon 66 to an elevated temperature, it may not be desirable to raise the temperature of the stent 110 and/or coating on the stent 110 to a temperature commensurate with the temperature of the balloon 66. For instance, raising the temperature of the stent 110 and/or coating of the stent 110 to a temperature greater than 30° C. in some instances, or raising the temperature of the stent 110 and/or coating of the stent 110 to a temperature greater than 40° C. in some instances, may adversely affect the performance and/or integrity of the stent 110 and/or coating of the stent 110.

As such, the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

During the crimping process, a cooling means or cooling source may be used to cool the crimping blades 14 of the crimping apparatus 10. For example, a cooling fluid C (e.g., a cooled fluid or a coolant) may be passed through the passage 40 of the crimping blades 14. The cooling fluid C may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 5° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection. In some embodiments, the cooling fluid C may be air, water, saline, perfluorocarbon, chlorofluorocarbon, hydrochlorofluorocarbon, carbon dioxide, nitrogen, or other desired fluid having a desired thermal conductivity. In some embodiments, the cooling fluid C may be continuously or periodically circulated through the crimping blades 14 to cool the crimping blades 14 to extract heat energy from the crimping blades 14 and thus cool the crimping blades 14.

As shown in FIG. 10B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 10B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 10B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 10B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 10C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, the electromagnetic energy 96 may be discontinued and/or the cooling fluid C may be discontinued. In some embodiments, however, it may be desired to continue to introduce the cooling fluid C through the crimping blades 14 as additional stents 110 are subsequently crimped to a balloon 66 of a balloon catheter 60 using the crimping apparatus 10. Thus, in such embodiments the crimping blades 14 may continuously be cooled by the fluid C throughout multiple stent crimping cycles. Prior to crimping another stent 110 onto a balloon 66 of another balloon catheter 60, the electromagnetic energy 96 may be propagated toward the next balloon catheter 60 to heat the balloon 66.

Figure 11A:
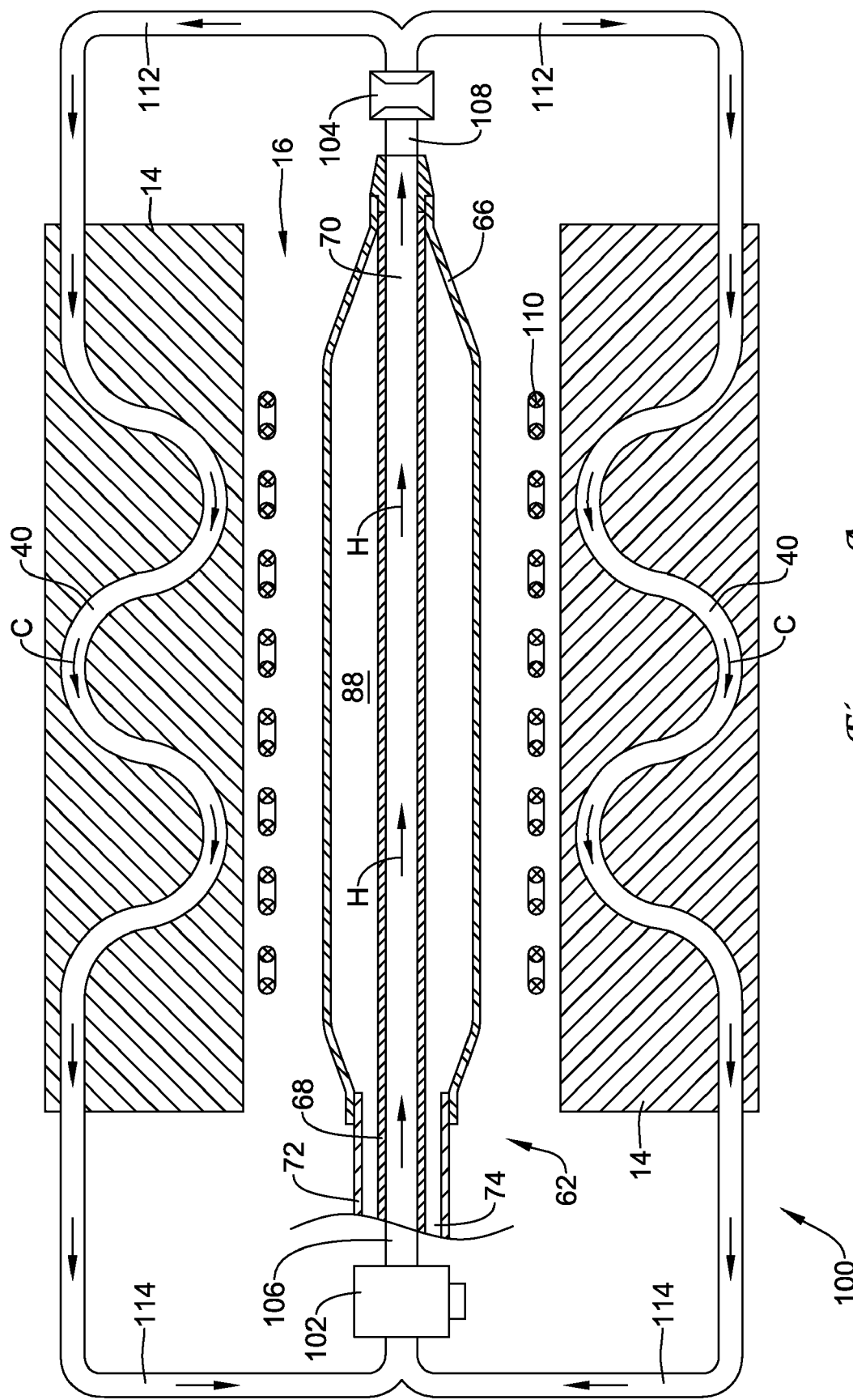
FIGS. 11A through 11C illustrate another exemplary crimping process in which a heat pump system is used to heat the balloon and cool the crimping elements.
Figure 11B:
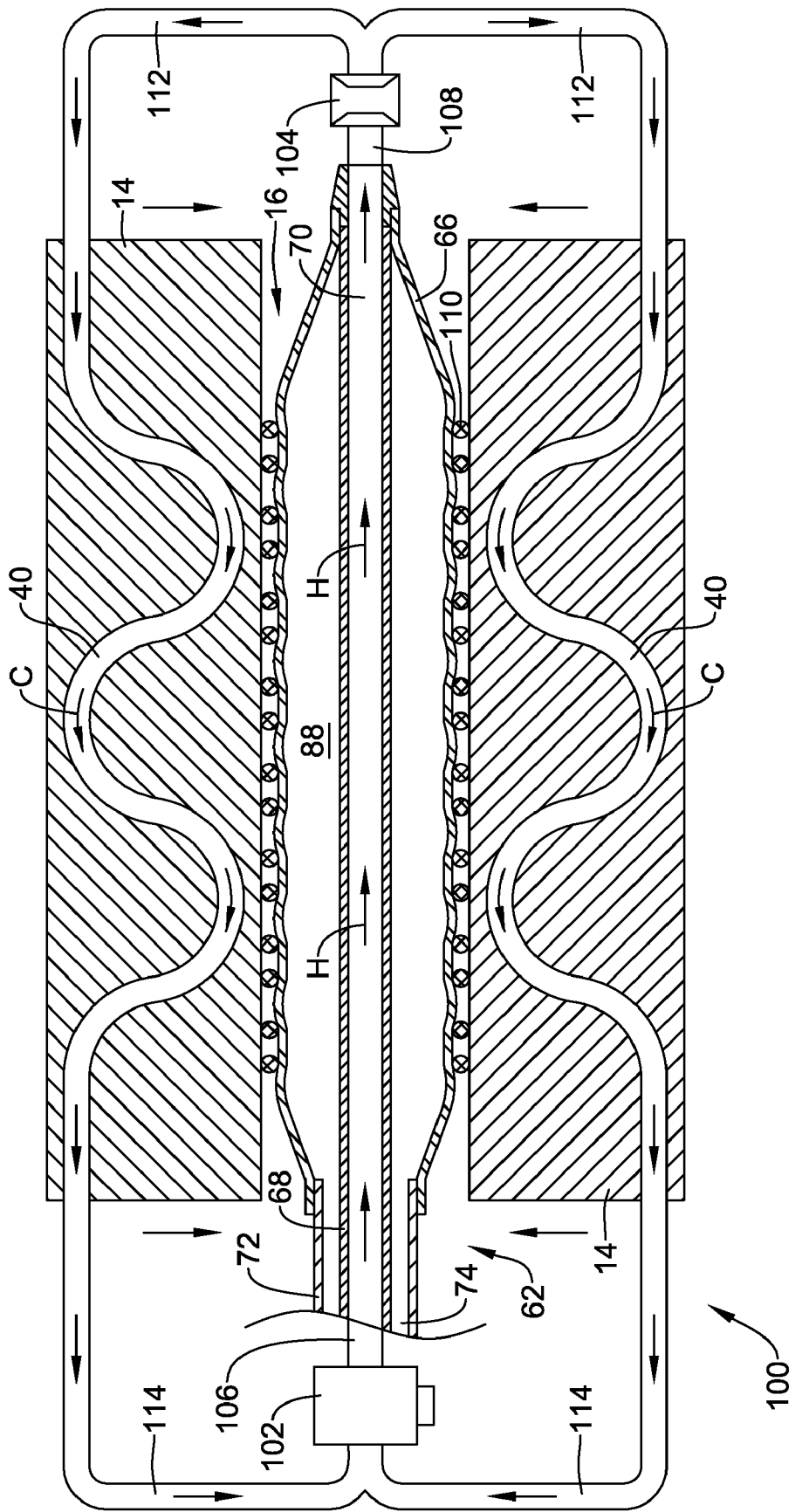
Figure 11C:
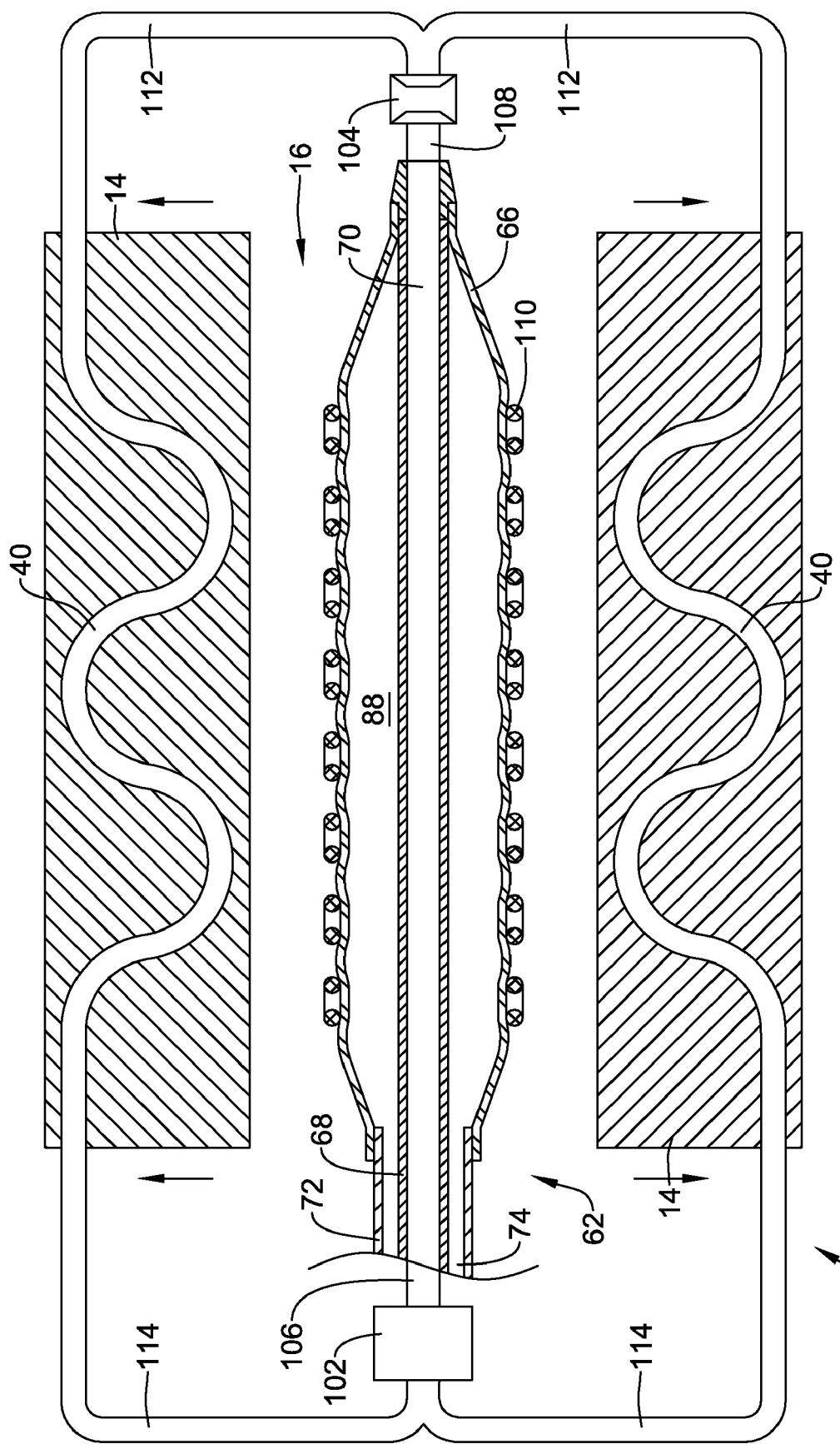

Another exemplary crimping process for crimping a stent 110 onto the inflation balloon 66 of the balloon catheter 60 is illustrated in FIGS. 11A-11C. Similar to that discussed above, the stent 110 may be any desired stent and may include a coating (e.g., a drug eluting coating, a protective coating, etc.), such as an abluminal coating or a conformal coating.

As shown in FIG. 11A, prior to crimping the stent 110 onto the balloon 66, the distal portion of the balloon catheter 60 is positioned within the crimping lumen 16 of the crimping apparatus 10. The stent 110 may be loaded onto the balloon 66 such that the stent 110 surrounds the central portion of the balloon 66. The stent 110 may be loaded onto the balloon 66 prior to or subsequent to placing the distal portion of the balloon catheter 60 in the crimping lumen 16 of the crimping apparatus 10. In some embodiments a crimping sleeve may be placed over the stent 110 during the crimping process.

During the crimping process, the inflation balloon 66 may be heated to an elevated temperature, such as at or above a glass transition temperature of the balloon material, causing the balloon material to soften and thus more easily conform to the contours of the stent 110. For instance, as shown in FIGS. 11A and 11B, the crimping apparatus 10 including the crimping blades 14 and the balloon catheter 60 may be included in a heat pump system 100, such as a heat exchanging system or other thermodynamic cycle, to provide the desired heating of the balloon 66 and/or cooling of the crimping blades 14. The heat pump system 100 may include a compressor 102 which may compress a fluid flowing through the heat pump system 100 prior to introducing the compressed fluid through the catheter shaft 62, and the heat pump system 100 may include an expansion valve 104 allowing the fluid to expand upon exiting the catheter shaft 62 and/or prior to being introduced through the crimping blades 14. Compression of the fluid generates heat energy in the fluid (e.g., increases the temperature of the fluid) providing a heating fluid H which may be introduced into the catheter 60 to heat the balloon 66. The compressed heating fluid H may be discharged from the compressor 102 and flowed into the interior of the catheter 60, for example, through the guidewire lumen 70 of the catheter shaft 62 through the compressor outlet conduit 106. In some embodiments, the compressed heating fluid H may have a temperature greater than the glass transition temperature of the balloon material in order to sufficiently heat the balloon material. For instance, in some embodiments, the heating fluid H may have a temperature greater than 40° C., greater than 45° C., greater than 50° C., greater than 55° C., greater than 60° C., or greater than 70° C. As the heating fluid H passes through the guidewire lumen 70, heat energy from the heating fluid H may be transferred to the inflation balloon 66, thus heating the inflation balloon 66 through conduction and/or convection. In some embodiments it may be desirable to heat the balloon 66 to a temperature greater than 40° C., greater than 45° C., or greater than 50° C. For example, in some embodiments it may be desirable to heat the balloon 66 to a temperature in the range of about 40° C. to about 60° C., or in the range of about 45° C. to about 50° C. during the crimping process.

As the heating fluid H exits the interior of the catheter 60 (e.g., exits the guidewire lumen 70) through the fluid outlet conduit 108, the heating fluid H is passed through the expansion valve 104 where the fluid expands. Expansion of the fluid through the expansion valve 104 cools the fluid (e.g., reduces the temperature of the fluid), providing a cooling fluid C which may be introduced into the passage 40 of the crimping blades 14 via the conduits 112. In some embodiments, the cooling fluid C, upon expansion, may have a temperature less than the temperature that the stent 110 and/or coating of the stent 110 is desired to be maintained at or below. For instance, in some embodiments, the cooling fluid C may have a temperature less than 40° C., less than 30° C., less than 20° C., less than 10° C., less than 5° C., or less than 0° C. When the temperature of the cooling fluid C is less than the temperature of the crimping blades 14, heat energy from the crimping blades 14 may be transferred to the cooling fluid C, thus cooling (e.g., lowering the temperature of) the crimping blades 14 during the crimping process through conduction and/or convection.

As the cooling fluid C exits the crimping blades 14 via the conduits 114, the cooling fluid C is delivered back to the compressor 102 such that the fluid may be heated through compression and circulated through the system 100 again. Thus, it can be seen that a fluid may be circulated through the catheter 60 and the crimping blades 14 of the crimping apparatus 10 during a crimping process in order to simultaneously heat the balloon 66 of the catheter 60 (e.g., add heat energy to the balloon 66) and cool the crimping blades 14 of the crimping apparatus (e.g., remove heat energy from the crimping blades 14).

As mentioned previously, it may be desirable to heat the balloon 66 to an elevated temperature, while not raising the temperature of the stent 110 and/or coating on the stent 110 to a temperature commensurate with the temperature of the balloon 66. As such, the heat pump system 100 coupled to the catheter 60 and the crimping apparatus 10 may be configured to maintain the temperature of the stent 110 and/or coating of the stent 110 at a temperature less than 40° C. in some embodiments, or may maintain the temperature of the stent 110 and/or coating of the stent 110 at a temperature less than 30° C. in some embodiments throughout the crimping process, even while the balloon material is heated to an elevated temperature greater than the temperature of the stent 110 and/or coating of the stent 110.

As shown in FIG. 11B, during the crimping process, the crimping blades 14 may be actuated to reduce the diameter of the crimping lumen 16 to thus crimp (i.e., radially compress) the stent 110 onto the balloon 66 of the balloon catheter 60. Crimping the stent 110 onto the balloon 66 causes the stent 110 to contact the balloon 66. In embodiments in which the balloon 66 is heated to an elevated temperature, there may be a tendency for heat energy in the balloon material to be transferred to the stent 110 and/or coating on the stent 110. However, as shown in FIG. 11B, passing a cooling fluid C through the passage 40 of the crimping blades 14 transfers heat energy from the crimping blades 14 to the cooling fluid C. The cooled crimping blades 14, which may be in direct contact with the stent 110 and/or coating of the stent 110 or indirectly in contact with the stent 110 and/or coating of the stent 110 via a crimping sleeve disposed about the stent 110 during the crimping process, may extract heat energy from the stent 110 and/or the coating of the stent 110. By cooling the crimping blades C to a temperature less than the elevated temperature of the balloon material, the temperature gradient allows heat transferred from the balloon 66 to the stent 110 and/or coating of the stent 110 to be transferred to the crimping blades 14. Thus, by cooling the crimping blades 14, for example by passing the cooling fluid C through the passage 40 of the crimping blades 14, the stent 110 and/or coating of the stent 110 may be maintained at a temperature less than the temperature attained by the material of the balloon 66 during the crimping process.

Thus, as the stent 110 is being crimped onto the balloon 66 of the balloon catheter 60, as shown in FIG. 11B, the balloon 66 may be heated to an elevated temperature, such as a temperature equal to or greater than a glass transition temperature of the material of the balloon 66. For instance, during the crimping process, the balloon 66 may be heated to a temperature greater than 40° C., greater than 45° C., or greater than 50° C.

Furthermore, as the stent 110 is being crimped onto the balloon 66 of the balloon catheter 60, as shown in FIG. 11B, the temperature of the stent 110 and/or the coating of the stent 110 may be maintained below the temperature attained by the balloon 66. For instance, during the crimping process, the stent 110 and/or the coating of the stent 110 may be maintained at and/or cooled to a temperature less than 40° C., or less than 30° C.

Thus, it can been seen that the stent 110 and/or the coating of the stent 110 may be cooled by the heat pump system 100 coupled to the crimping apparatus 10 simultaneously as the balloon 66 is being heated during a crimping process in which the stent 110 is being crimped onto the balloon 66 of the balloon catheter 60. In other words, while the crimping apparatus 10 is being actuated radially inward in contact with (direct or indirect) the stent 110 to compress the stent 110 onto the balloon 66 and/or while the crimping apparatus 10 maintains a crimping force on the stent 110 for a duration of time during the crimping process, the balloon 66 may be heated to an elevated temperature while the temperature of the stent 110 and/or coating of the stent 110 is maintained at a temperature (e.g., cooled) notably less than the temperature of the balloon 66.

As shown in FIG. 11C, once the stent 110 has been crimped onto the balloon 66 of the balloon catheter 60, the crimping blades 14 may be actuated to enlarge the diameter of the crimping lumen 16 in order to remove the crimped stent 110 and balloon 66 from the crimping apparatus 10. At this point in the crimping process, circulation of the heating fluid H may be discontinued and/or circulation of the cooling fluid C may be discontinued. Prior to crimping another stent 110 onto a balloon 66 of another balloon catheter 60, the heat pump system 100 may be coupled to the next balloon catheter 60 to heat the balloon 66 while cooling the crimping blades 14.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of crimping a stent onto a balloon of a balloon catheter, comprising:
   providing a crimping apparatus including a plurality of crimping elements forming a crimping lumen having a diameter, wherein the plurality of crimping elements are actuatable to alter the diameter of the crimping lumen;
   providing a balloon catheter including an elongate shaft and an inflation balloon secured to a distal region of the elongate shaft;
   providing a stent;
   positioning the stent around the inflation balloon of the balloon catheter;
   situating the stent and the inflation balloon of the balloon catheter within the crimping lumen;
   crimping the stent onto the inflation balloon of the balloon catheter with the crimping apparatus;
   heating the inflation balloon to a temperature greater than 40° C. while crimping the stent onto the inflation balloon of the balloon catheter; and
   maintaining the crimping elements at a temperature less than 40° C. while crimping the stent onto the inflation balloon of the balloon catheter.

2. The method of claim 1, wherein the stent includes a drug eluting coating, wherein the drug eluting coating is maintained at a temperature less than 40° C. while crimping the stent onto the inflation balloon of the balloon catheter.

3. The method of claim 1, wherein the stent includes a fenestrated framework, wherein the fenestrated framework of the stent is maintained at a temperature less than 40° C. while crimping the stent onto the inflation balloon of the balloon catheter.

4. The method of claim 1, wherein the elongate shaft includes an inflation lumen in fluid communication with an interior of the inflation balloon, wherein a heated fluid is introduced through the inflation lumen into the inflation balloon to heat the inflation balloon.

5. The method of claim 1, wherein the elongate shaft includes a guidewire lumen, wherein a heated fluid is introduced through the guidewire lumen to heat the inflation balloon.

6. The method of claim 1, wherein the elongate shaft includes a guidewire lumen, wherein a mandrel inserted through the guidewire lumen is heated to heat the inflation balloon.

7. The method of claim 6, wherein the mandrel includes a ferromagnetic material and the mandrel is exposed to an alternative magnetic field to heat the mandrel.

8. The method of claim 6, wherein the mandrel is heated by resistance heating.

9. The method of claim 1, wherein an interior of the inflation balloon includes a moisture rich environment, and wherein the inflation balloon is exposed to microwave energy to heat the inflation balloon.

10. The method of claim 1, wherein the inflation balloon includes a moisture rich layer responsive to electromagnetic energy and wherein the inflation balloon is exposed to electromagnetic energy to heat the inflation balloon.

11. The method of claim 1, further comprising a heat pump system including a compressor, wherein a compressed fluid from the compressor is circulated through the elongate shaft of the balloon catheter to heat the inflation balloon, and wherein the compressed fluid is allowed to expand upon exiting the elongate shaft of the balloon catheter.

12. The method of claim 11, wherein the expanded fluid is passed through a passage through one or more of the crimping elements of the crimping apparatus.

13. The method of claim 1, wherein one or more of the plurality of crimping elements includes a passage extending therein, wherein a fluid is circulated through the passage to cool the crimping apparatus during the crimping step.

14. The method of claim 1, wherein one or more of the plurality of crimping elements are in contact with a body, wherein heat energy from the crimping elements is transferred to the body.

15. A method of crimping a stent onto a balloon of a balloon catheter, comprising:
   providing a crimping apparatus including a plurality of crimping elements forming a crimping lumen having a diameter, wherein the plurality of crimping elements are actuatable to alter the diameter of the crimping lumen;
   providing a balloon catheter including an elongate shaft and an inflation balloon secured to a distal region of the elongate shaft;
   providing a stent;
   positioning the stent around the inflation balloon of the balloon catheter;
   situating the stent and the inflation balloon of the balloon catheter within the crimping lumen;
   crimping the stent onto the inflation balloon of the balloon catheter with the crimping apparatus;
   cooling one or more of the plurality of crimping elements of the crimping apparatus while crimping the stent; and
   heating the inflation balloon of the balloon catheter while crimping the stent.

16. The method of claim 15, wherein the step of heating the inflation balloon of the balloon catheter includes introducing a heated fluid through the elongate shaft of the balloon catheter.

17. The method of claim 16, wherein the heated fluid introduced through the elongate shaft of the balloon catheter heats the inflation balloon to an elevated temperature greater than 40° C.

18. The method of claim 15, wherein the step of cooling one or more of the plurality of crimping elements includes introducing a cooled fluid through a passage in one or more of the plurality of crimping elements.

19. The method of claim 18, wherein the cooled fluid introduced through a passage in one or more of the plurality of crimping elements is circulated through a heat exchanger.

20. The method of claim 15, wherein the stent includes a drug eluting coating, and wherein the drug eluting coating is maintained at a temperature lower than the temperature attained by the inflation balloon throughout the crimping step.

21. The method of claim 15, wherein the stent includes a drug eluting coating, wherein a cooled fluid introduced through the passage of one or more of the plurality of crimping elements extracts heat energy from the drug eluting coating to maintain the drug eluting coating at a temperature below an elevated temperature attained by the inflation balloon.

22. The method of claim 21, wherein the drug eluting coating is maintained at a temperature of less than or equal to 30° C. throughout the crimping step.

23. The method of claim 22, wherein the elevated temperature attained by the inflation balloon is greater than 40° C.

24. A stent crimping system for crimping a stent onto a balloon of a balloon catheter, the stent crimping system including:
- a crimping apparatus including a plurality of actuatable crimping elements defining a crimping lumen;
- a balloon catheter including an elongate shaft and an inflation balloon;
- a stent disposed about the inflation balloon;
- a means for transferring heat energy to the inflation balloon such that the inflation balloon has a temperature greater than 40° C.; and
- a means for transferring heat energy from the plurality of crimping elements such that the plurality of crimping elements have a temperature less than 40° C.

25. The stent crimping system of claim 24, wherein the means for transferring heat energy from the plurality of crimping elements includes a fluid circulated through a fluid passage of at least one of the plurality of actuatable crimping elements.

26. The stent crimping system of claim 24, wherein the means for transferring heat energy from the plurality of crimping elements includes a body having a temperature less than 40° C., wherein the body is in contact with at least one of the plurality of actuatable crimping elements.

27. The stent crimping system of claim 24, wherein the means for transferring heat energy from the plurality of crimping elements includes an ambient environment having a temperature less than 10° C.

28. The stent crimping system of claim 24, wherein the means for transferring heat energy to the inflation balloon includes a microwave energy source.

29. The stent crimping system of claim 24, wherein the means for transferring heat energy to the inflation balloon includes a heated fluid within the elongate shaft of the balloon catheter.

30. The stent crimping system of claim 29, wherein the elongate shaft includes an inflation lumen in fluid communication with an interior of the inflation balloon, wherein the heated fluid is within the inflation lumen and the interior of the inflation balloon.

31. The stent crimping system of claim 29, wherein the elongate shaft includes a guidewire lumen, wherein the heated fluid is within the guidewire lumen.

32. The stent crimping system of claim 24, wherein the elongate shaft includes a guidewire lumen, and wherein the means for transferring heat energy to the inflation balloon includes a heated mandrel inserted through the guidewire lumen.

33. The stent crimping system of claim 32, wherein the heated mandrel includes a ferromagnetic material.

34. The stent crimping system of claim 24, wherein the means for transferring heat energy to the inflation balloon includes a compressed fluid within the elongate shaft of the balloon catheter.

* * * * *